(12) United States Patent
Wei

(10) Patent No.: US 11,278,666 B2
(45) Date of Patent: Mar. 22, 2022

(54) MEDICATION INFUSION DEVICE

(71) Applicant: Min Wei, Carmel, IN (US)

(72) Inventor: Min Wei, Carmel, IN (US)

(73) Assignee: Min Wei, Carmel, IN (US)

( * ) Notice: Subject to any disclaimer, the term of this patent is extended or adjusted under 35 U.S.C. 154(b) by 129 days.

(21) Appl. No.: 16/686,186

(22) Filed: Nov. 17, 2019

(65) Prior Publication Data

US 2020/0078513 A1 Mar. 12, 2020

Related U.S. Application Data

(63) Continuation of application No. 15/313,168, filed as application No. PCT/US2015/035015 on Jun. 10, 2015, now Pat. No. 10,532,151.

(60) Provisional application No. 62/016,737, filed on Jun. 25, 2014.

(51) Int. Cl.
| | |
|---|---|
| *A61M 5/00* | (2006.01) |
| *A61M 5/142* | (2006.01) |
| *A61M 5/145* | (2006.01) |
| *A61M 5/168* | (2006.01) |
| *A61M 5/158* | (2006.01) |

(52) U.S. Cl.
CPC .... *A61M 5/14244* (2013.01); *A61M 5/14526* (2013.01); *A61M 5/158* (2013.01); *A61M 5/16804* (2013.01); *A61M 5/16877* (2013.01); *A61M 2005/14513* (2013.01); *A61M 2005/1585* (2013.01)

(58) Field of Classification Search
CPC .......... A61M 5/14244; A61M 5/14526; A61M 5/158; A61M 5/16804; A61M 5/16877; A61M 2005/14513; A61M 2005/1585
See application file for complete search history.

(56) References Cited

U.S. PATENT DOCUMENTS

| | | | | |
|---|---|---|---|---|
| 6,375,638 | B2 * | 4/2002 | Nason | A61M 5/1452 604/131 |
| 6,723,072 | B2 * | 4/2004 | Flaherty | A61M 5/1452 604/131 |
| 7,922,694 | B2 * | 4/2011 | Harttig | A61M 5/14526 604/151 |
| 9,416,775 | B2 * | 8/2016 | Focht | F04B 7/06 |
| 10,821,239 | B2 * | 11/2020 | Hanson | A61M 5/14244 |
| 2002/0018720 | A1 * | 2/2002 | Carlisle | A61M 5/16881 417/26 |

(Continued)

*Primary Examiner* — Steven O Douglas
(74) *Attorney, Agent, or Firm* — Min Wei

(57) ABSTRACT

A medication infusion device includes a medication container containing liquid medication; an infusion needle; and a reciprocating pump having a pump chamber. The liquid medication is withdrawn from the medication container into the pump chamber during suction operation of the reciprocating pump, and the liquid medication is dispensed out of the pump chamber through the infusion needle during dispensing operation of the reciprocating pump. There are also mechanisms preventing liquid from flowing through the infusion needle during suction operation of the reciprocating pump and preventing liquid from flowing back into the medication container during dispensing operation of the reciprocating pump. The medication infusion device may further include a microcontroller to control medication infusion volume and rate.

11 Claims, 28 Drawing Sheets

(56) References Cited

U.S. PATENT DOCUMENTS

| | | | |
|---|---|---|---|
| 2004/0115067 A1* | 6/2004 | Rush | F04B 43/08 417/322 |
| 2011/0270188 A1* | 11/2011 | Caffey | A61M 5/14593 604/151 |
| 2016/0082182 A1* | 3/2016 | Gregory | A61M 5/14526 604/150 |

* cited by examiner

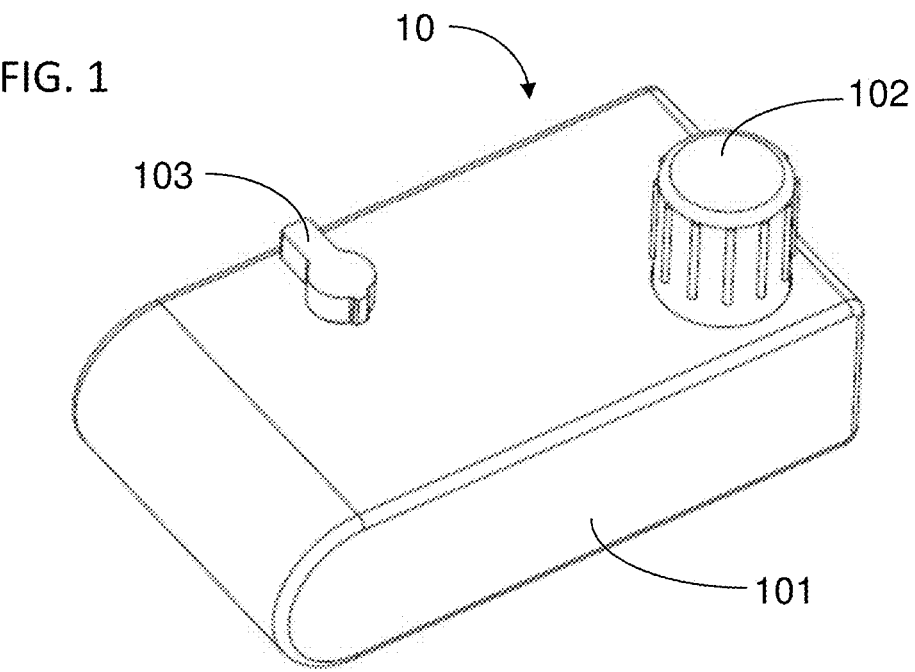
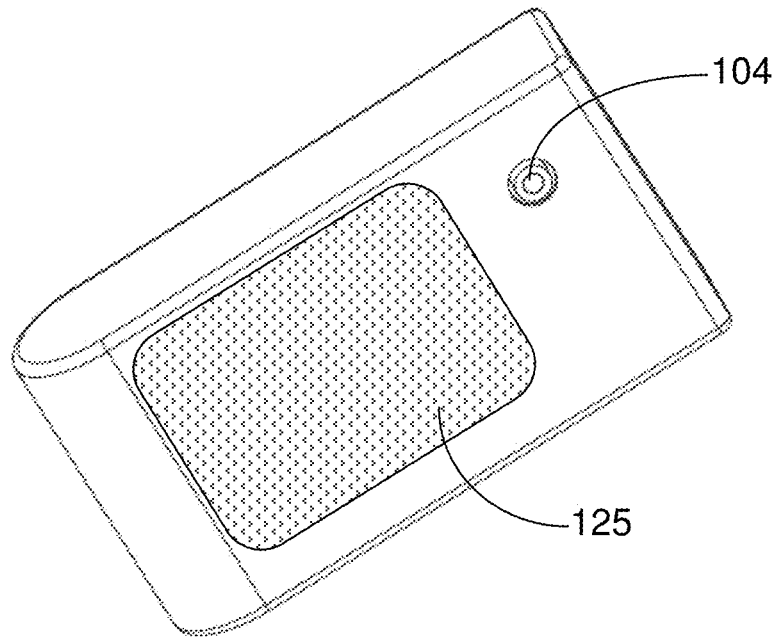

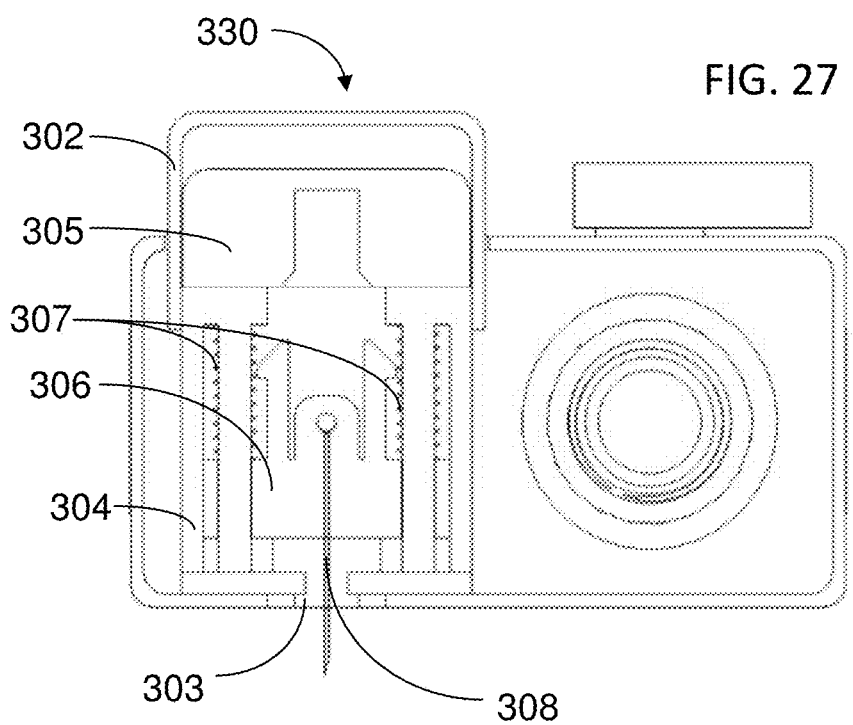
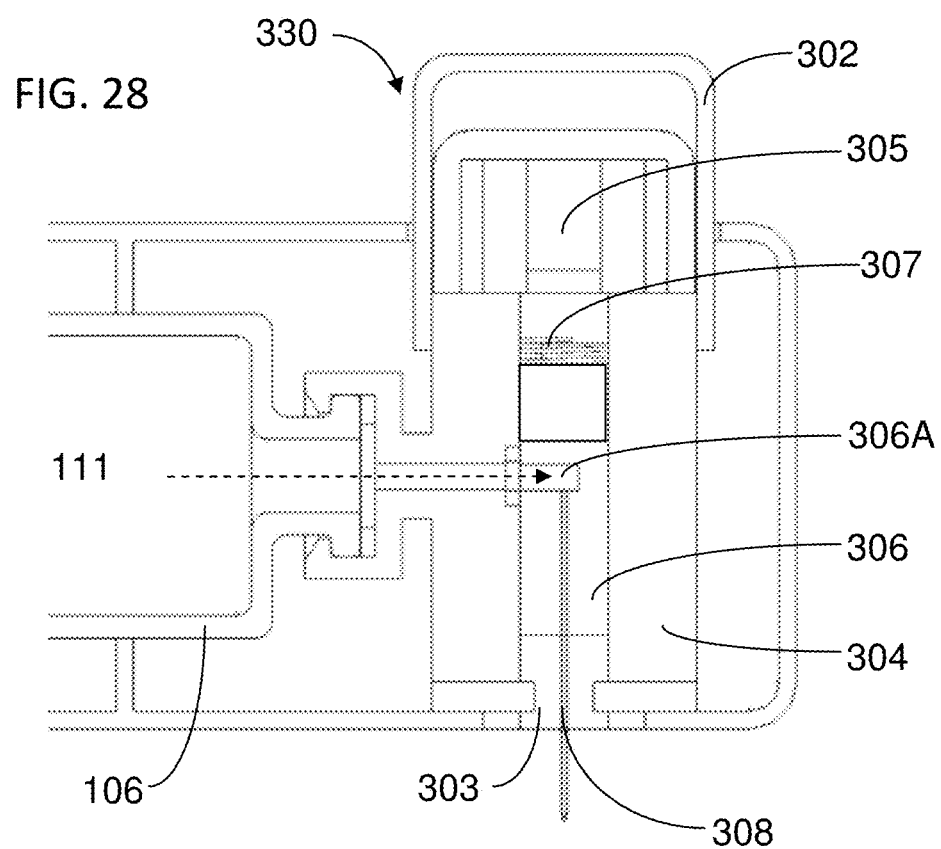

FIG. 47
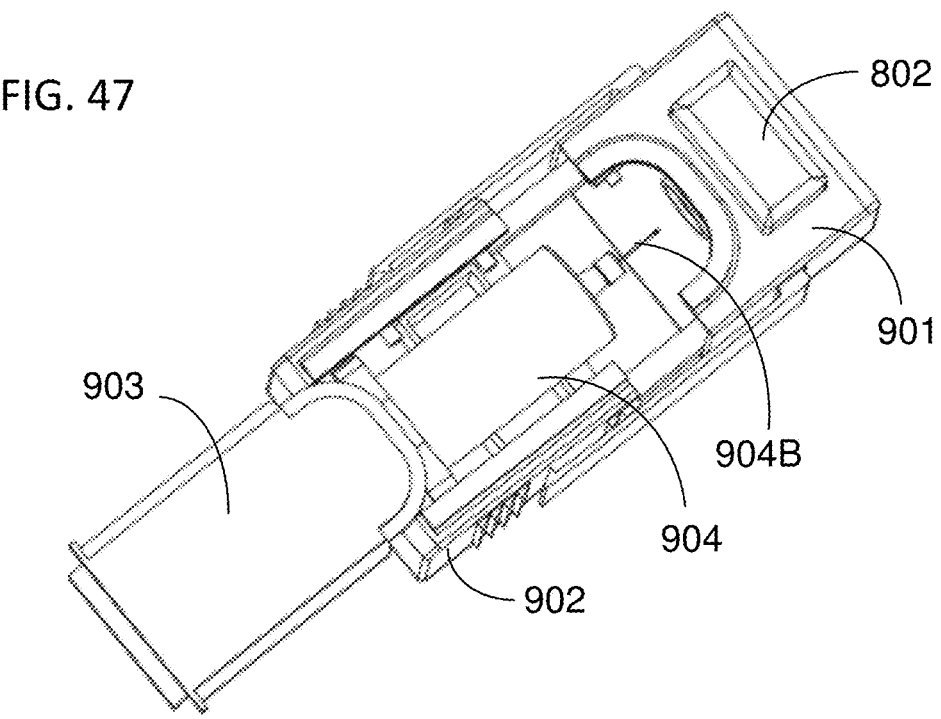
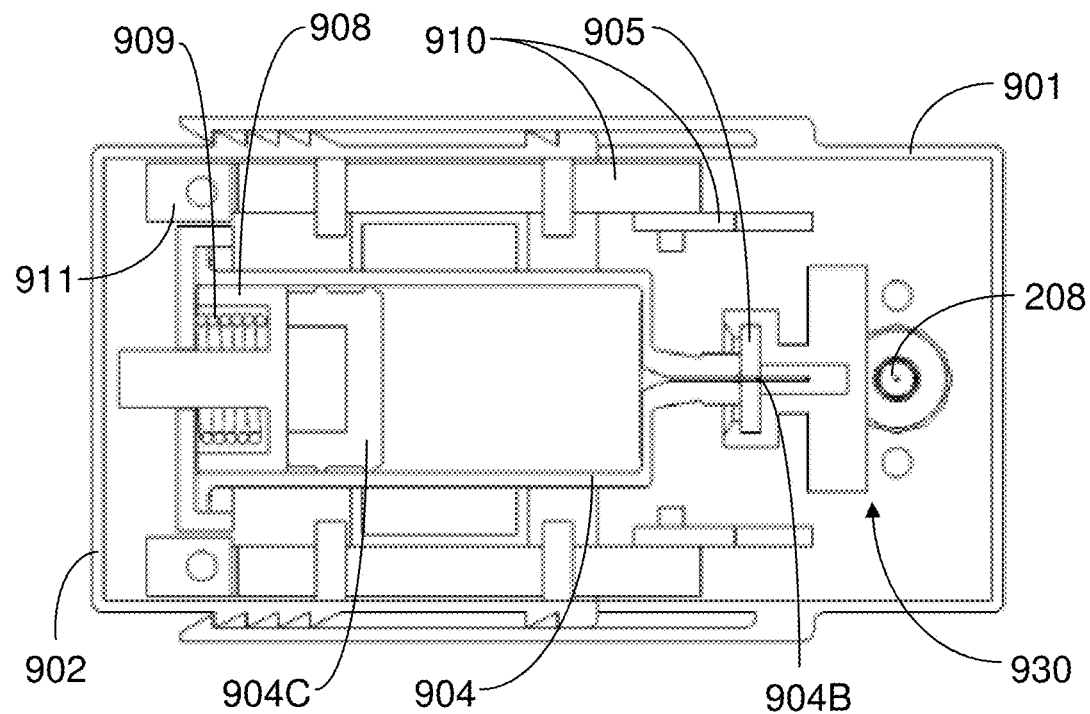
FIG. 48

MEDICATION INFUSION DEVICE

CROSS-REFERENCE TO RELATED APPLICATIONS

This application is a continuation of U.S. application Ser. No. 15/313,168, filed on Nov. 22, 2016, which is a 371 national stage of international application PCT/US15/35015, filed on Jun. 10, 2015, which claims the benefit of priority to U.S. provisional application No. 62/016,737, filed on Jun. 25, 2014. The disclosures of all these prior-filed applications are incorporated by reference herein in their entireties.

TECHNICAL FIELD

The invention relates to an infusion device for delivering liquid medications.

BACKGROUND OF THE INVENTION

External drug injection/infusion devices are typically used to deliver substances which therapeutic compounds that cannot be delivered effectively when administered orally. Delivering large volume of such therapeutic compounds, for example, greater than two milliliter, may cause pain and/or tissue damage if the procedure is completed within short period of time, for example, 15 seconds. Protein drugs are exemplary therapeutic agents that are more ideal when delivered at slow rates if large delivery volume is required. In such circumstance, wearable, patch-type infusion devices are better options than bolus injection devices. In use, these wearable, patch-type infusion devices are mounted onto the skin or clothing of a patient and triggered to deliver the therapeutic compound(s) into the patient.

Many wearable, patch-type infusion devices for a variety of therapeutic compounds have been patented or are being developed by different entities. These include among others: Abbott wearable infusion device for controlled delivery of therapeutic agents, patent application U.S. Patent Publication No. 2012/0022499 (Anderson, et al.); Beckton Dickinson MicroInfusor™ (WO 2011/075105 (Peterson, et al.)); Calibra Medical Finesse Insulin Patch-Pen; Elan fully disposable MEDIPAD patch pump (U.S. Pat. No. 5,527,288 (Gross, et al.) and following patents); Insulet Corporation (USA) OmniPod System Patch insulin pump; Roche Medingo Solo Patch Pump (WO 2010/041260 (Yodfat, et al.)); Roche single-use electromechanical injection device (SID) developed specifically for use with the trastuzumab SC fixed-dose formulated with recombinant human hyaluronidase (U.S. Patent Publication No. 2011/0166512 (Both, et al.)); Novo Nordisk skin mountable insulin patch pump (U.S. Patent Publication No. 2011/0137255 (Nielsen, et al.)); West SmartDose patch pump (Application US 2009/0093793 (Gross, et al.)).

Conventionally, patch-type infusion devices are typically filled by a patient prior to use. Recently, some advancement in this field has shown the feasibility of using pre-filled medication containers. The pre-filled medication containers contain medication formulations in sterile form, which requires sterilized infusion needle. To keep the infusion needle sterile, current patch-type infusion device designs either require one or more secondary sterile packagings to maintain sterility if the infusion needle exposed inside the infusion device before using the infusion device. In this situation, after the sterile barriers (secondary packaging) are removed, the needle is open to air. According to U.S. Centers for Disease Control and Prevention (CDC), the longer a sterile item is exposed to air, the greater the number of microorganisms that will settle on it. And eventually, the sterile item, for example, pre-sterilized needle, will eventually become contaminated. The contaminated needle can not only cause infection and disease transmission, but also change properties of therapeutic reagents. If the sterile barrier is required to be removed by user, especially patient without medical training, it is likely that sterile infusion needle and therapeutic reagent are contaminated due to uncontrolled period of have the infusion needle exposed to open air. Therefore, it is preferable to have a device design that keeps the infusion needle sterile until the needle is inserted into user body. Furthermore, manually removing tight seal sterile barrier(s) is inconvenient and sometime difficult for end users, especially for patients with impaired vision and dexterity issues. Therefore, there is a need in better design to make the wearable, patch-type infusion devices easier to use.

SUMMARY OF THE INVENTION

It is an object of the present invention to provide an easy-to-use, wearable, patch-type automatic infusion device. This invention presents a series of the designs for the infusion device comprising: 1) a pre-filled medication container; 2) a mechanical driven needle insertion mechanism containing a sterile infusion needle that is fully enclosed in a sterile environment until the infusion needle is inserted into infusion site on user body; 3) a means that delivers medication from the medication container into the infusion site through the infusion needle. This invention is to overcome one or more of the disadvantages of the prior art.

It is an advantage of the present invention that the wearable, patch-type infusion device embodiments here have a sterile infusion needle that is fully enclosed in a sterile environment until the infusion needle is inserted into infusion site on user body so that there is no risk of sterility breach due to damage of secondary packaging. Such an arrangement also minimizes the potential for particles from environment to be transferred into the infusion needle.

It is an advantage of the present invention that the wearable, patch-type infusion device embodiments here have an automatic needle insertion mechanism that do not require user to remove tight sealed secondary packaging.

It is an advantage of the present invention that the wearable, patch-type infusion device embodiments here have a medication container that is pre-filled so that users don't have to manually fill the medication container.

It is a further advantage that the present invention that the wearable, patch-type infusion device embodiments here have the medication container and the needle insertion mechanisms, which can be assembled with a variety of drug delivery means, including mechanical spring force, force generated from osmotic potential, force generated from chemical reaction, force generated from compressed air, hydraulic force, electromechanical force or of another type.

Exemplary embodiments provide wearable, patch-type infusion devices that may adhere to the skin or clothing of the patient and deliver a therapeutic agent into the patient by infusion at slow flow rates. The slow infusions achieved by exemplary devices minimize the pain sensation and tissue damage associated with a volume of a therapeutic agent entering into the patent's tissue. Exemplary time durations for slow delivery achieved by exemplary infusion devices may range from about 10 second to about 24 hours, but are not limited to this exemplary range. Exemplary volumes of therapeutic agent deliverable by exemplary devices may range from about 1 milliliters to about 50 milliliter, but are not limited to this exemplary range.

BRIEF DESCRIPTION OF THE DRAWINGS

The figures are schematic and simplified for clarity, and they just show details, which are essential to the understanding of the invention, while other details are left out. Throughout, the same reference numerals are used for identical or corresponding parts.

FIG. 1 and FIG. 2 are perspective views of an exemplary infusion device assembly according to the invention.

FIG. 25, FIG. 26, FIG. 27 and FIG. 28 show cross-sectional views of the needle insertion mechanism of the second alternative infusion device assembly according to the invention.

FIG. 47 shows the assembling of the pre-filled syringe into the eighth alternative infusion device assembly according to the invention.

FIG. 48 shows a cross-sectional view of the eighth alternative infusion device assembly according to the invention.

Corresponding parts are marked with the same reference symbols in all figures.

DETAILED DESCRIPTION OF THE INVENTION

Figure 3:
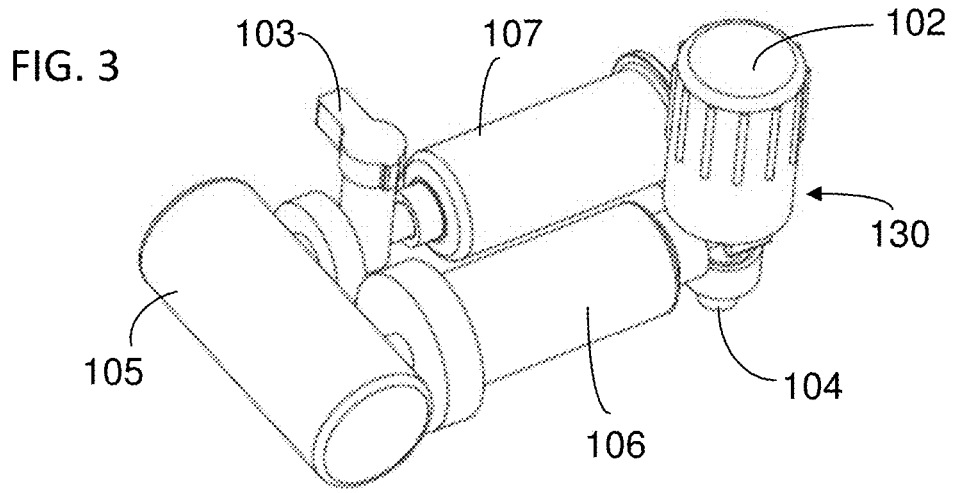
FIG. 3 is a perspective view of the internal components of the exemplary infusion device assembly according to the invention.
Figure 4:
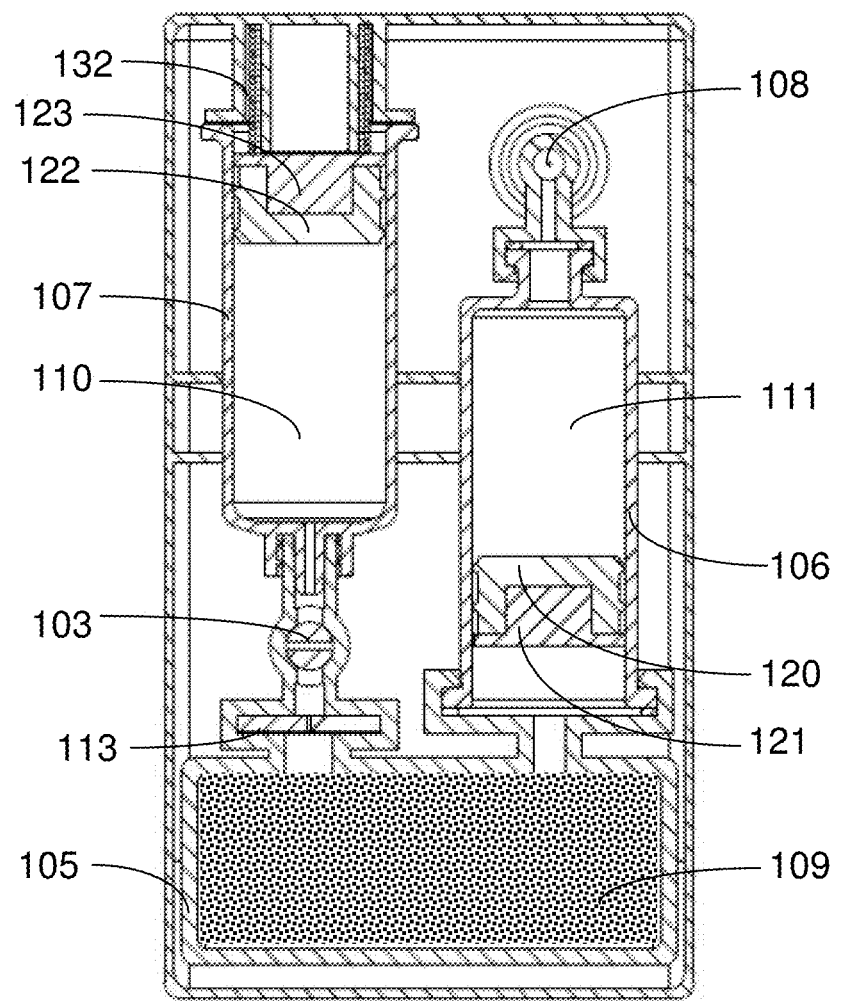
FIG. 4 shows a cross-sectional view of the exemplary infusion device assembly according to the invention.
Figure 5:
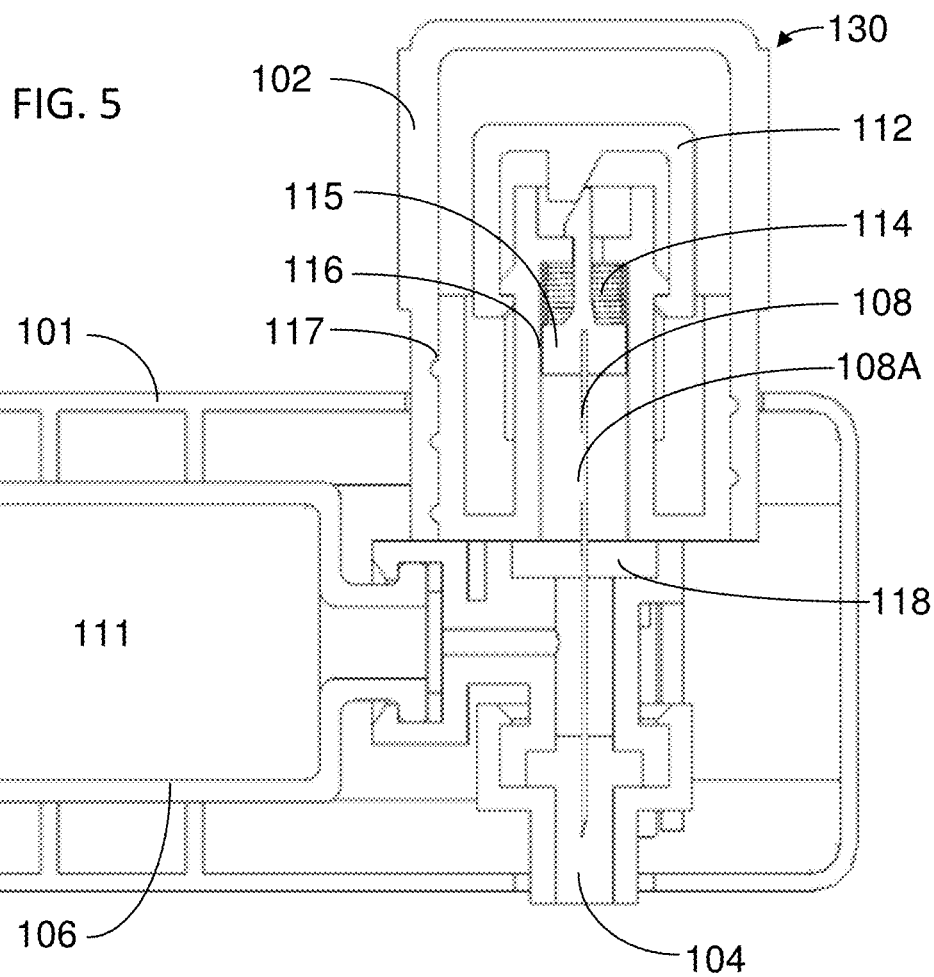
FIG. 5 shows a cross-sectional view of the needle insertion mechanism of the exemplary infusion device assembly according to the invention.
Figure 6:
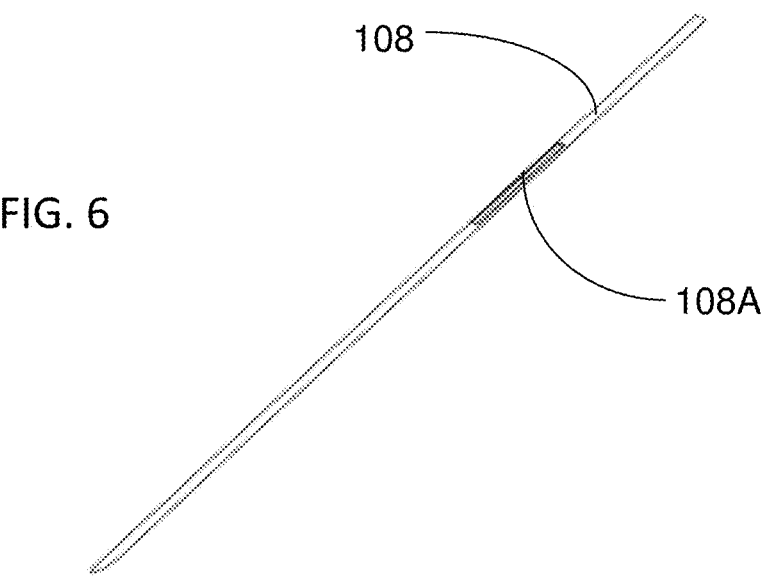
FIG. 6 shows an infusion needle, with a side port, used in the needle insertion mechanism of the exemplary infusion device assembly according to the invention.
Figure 7:
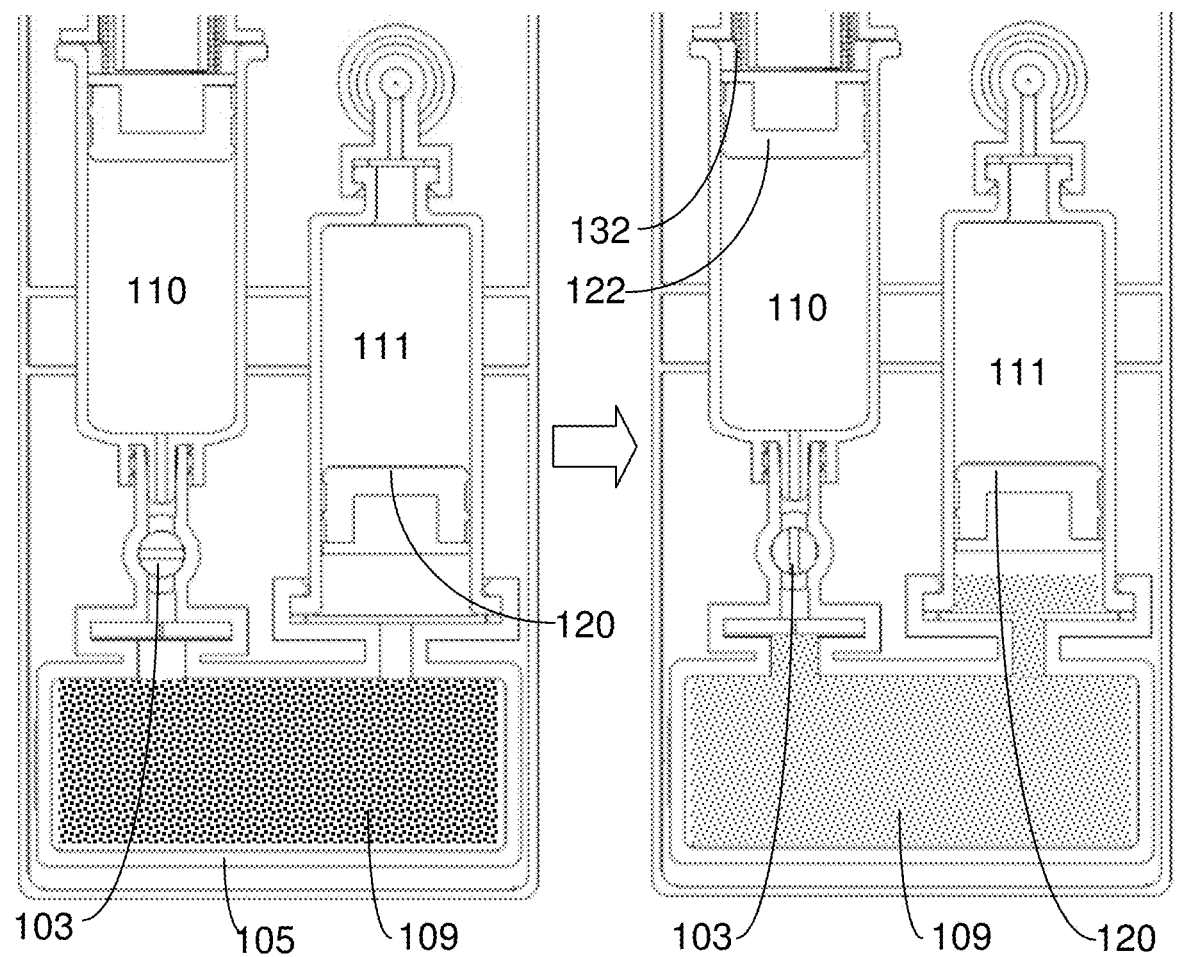
FIG. 7 shows a series of cross-sectional views illustrating an osmotic pressure based medication delivery mechanism of the infusion device assembly according to the invention.
Figure 8:
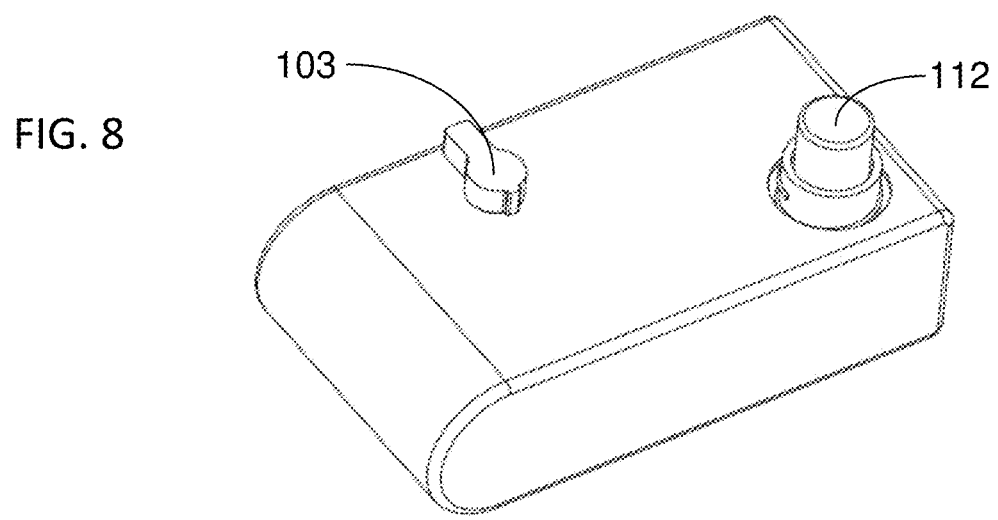
FIG. 8 is a perspective view of the infusion device assembly after a protection cap is removed according to the invention.
Figure 9:
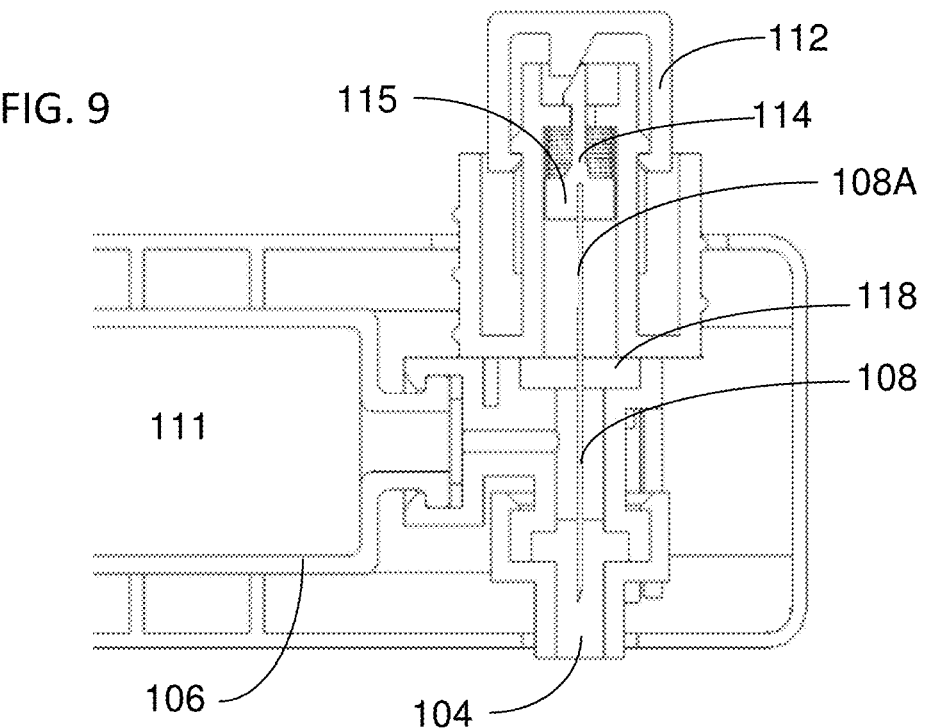
FIG. 9 and FIG. 10 show cross-sectional views of the needle insertion mechanism of the infusion device assembly according to the invention.
Figure 10:
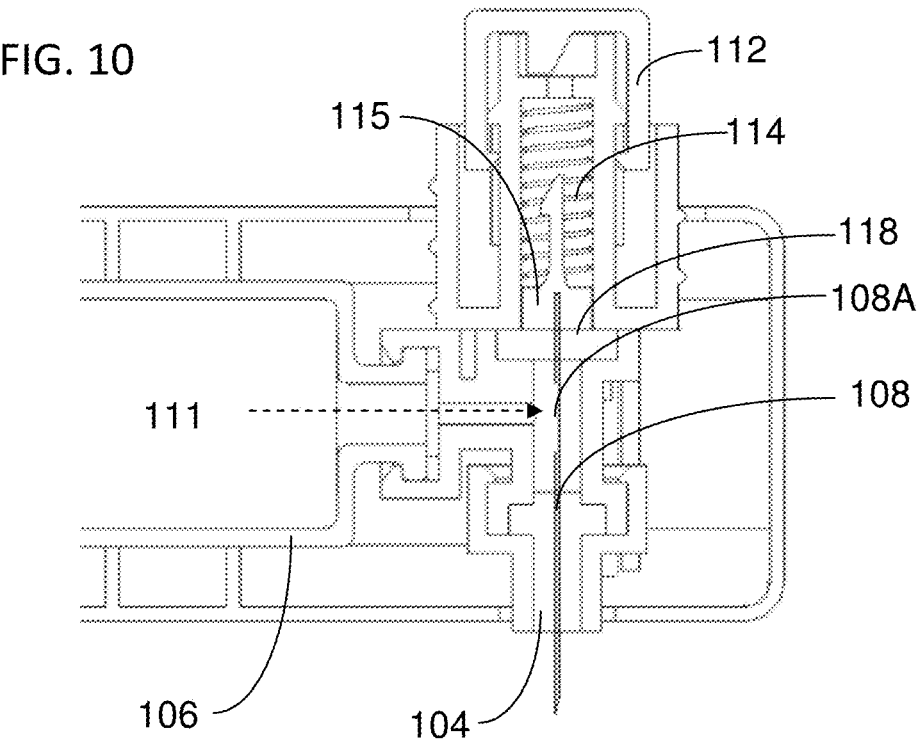

The present invention will become more fully understood from the detailed description given hereinbelow and the accompanying drawings which are given by way of illustration only, and thus, are not limitive of the present invention, and wherein:

The apparatus and methods presented herein can be used for delivering any of a variety suitable therapeutic agents or substances, such as a drug, into a patient. Initially it may be convenient to define that, the term "distal end" or "insertion end" of a infusion needle is meant to refer to the end of the infusion needle inserted into the patient. The words "upper", "lower", "right" and "left" designate directions in the drawings to which reference is made. The words "inward" and "outward" refer to directions toward and away from, respectively, FIGS. 1-10 illustrate the construction and function mechanism of an exemplary infusion device assembly 10 according to the invention. With reference to FIGS. 1, 2 and 3, the exemplary injection device assembly 10 has major components including a housing 101, a fluid control switch 103, a pre-filled medication container 106, a water container 107, an osmotic chamber 105 and a needle insertion mechanism 130. With reference to FIG. 2, an adhesive layer 125 is used to attach the infusion device assembly 10 at the infusion site. As an alternative, straps can be used as the body attachment means instead of the adhesive layer 125. With reference to FIG. 4, the water container 107 contains water 110 and the water 110 is sealed by a movable piston 122. The movable piston 122 is backed by a rigid plate 123, and the rigid plate 123 is biased against a compression spring 132. The fluid control switch 103 controls the water 110 flowing from the water container 107 into the osmotic chamber 105 through a semi-permeable membrane 113. The osmotic chamber 105 contains osmotic reagent 109. The medication container 106 contains liquid medication 111. The liquid medication 111 is sealed by a movable piston 120 backed by a rigid plate 121. When the movable piston 120 is pushed up, the liquid medication 111 will be delivered through an infusion needle 108. With reference to FIG. 5, the needle insertion mechanism 130 has major components including a protection cap 102, an activation button 112, a needle driver 115, a needle driving spring 114, interference type sealing features 116 and 117, pierceable elastomeric septa 118 and 104, and the infusion needle 108 with side port feature 108A. The sealing features 116 and 117, the pierceable elastomeric septa 118 and 104 all together keep the sterility for the infusion needle 108 and the liquid medication 111. FIG. 6 further illustrates the infusion needle 108 with side port feature 108A. With reference to FIG. 7, when the fluid control switch 103 is turned at "off" position, the water 110 is restrained in the water container 107. When the fluid control switch 103 is turned at "on" position, the water 110, pushed by the movable piston 122 and the compression spring 132, flows into the osmotic chamber 105 through the semi-permeable membrane 113. Because the water 110 flows into the osmotic chamber 105, the osmotic reagent 109 swells and pushes the rigid plate 121 and the movable piston 120 up. Consequently, the liquid medication 111 is expelled out of the medication container 106. The amount of medication infused can be controlled by turning the fluid control switch 103. With reference to FIG. 8, the protection cap 102 is removed and the activation button 112 is exposed before infusion. With reference to FIGS. 9 and 10, at the beginning of the medication infusion, user pushes down the activation button 112, the downward movement of the activation button 112 causes releasing of the needle driver 115. Then, the needle driving spring 114 pushes the needle driver 115 and the infusion needle 108 downward. During the downward movement of the infusion needle 108, the side port feature 108A on the infusion needle pierces through the elastomeric septum 118 and establishes fluid path with the medication container 106, so that the liquid medication 111 can flow through the needle side port feature 108A into the infusion needle 108. The dash line with arrow in FIG. 10 indicates the fluid path of the liquid medication 111 during medication infusion. Also during the downward movement of the infusion needle 108, the distal end of the infusion needle 108 pierces through the pierceable septum 104 and insert into body site for medication infusion.

Figure 11:
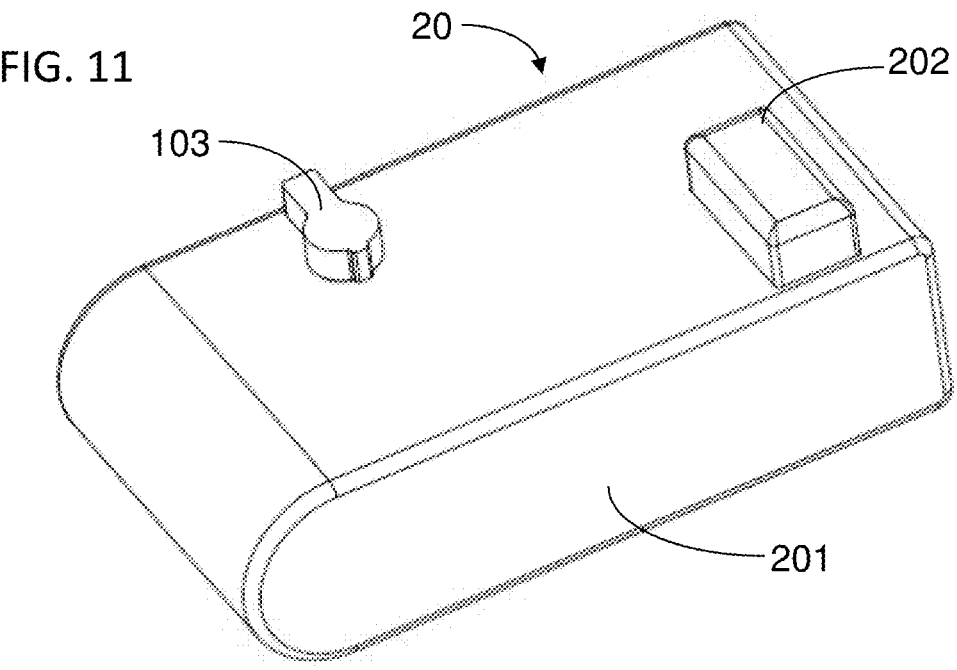
FIG. 11 and FIG. 12 are perspective views of the first alternative infusion device assembly according to the invention.
Figure 12:
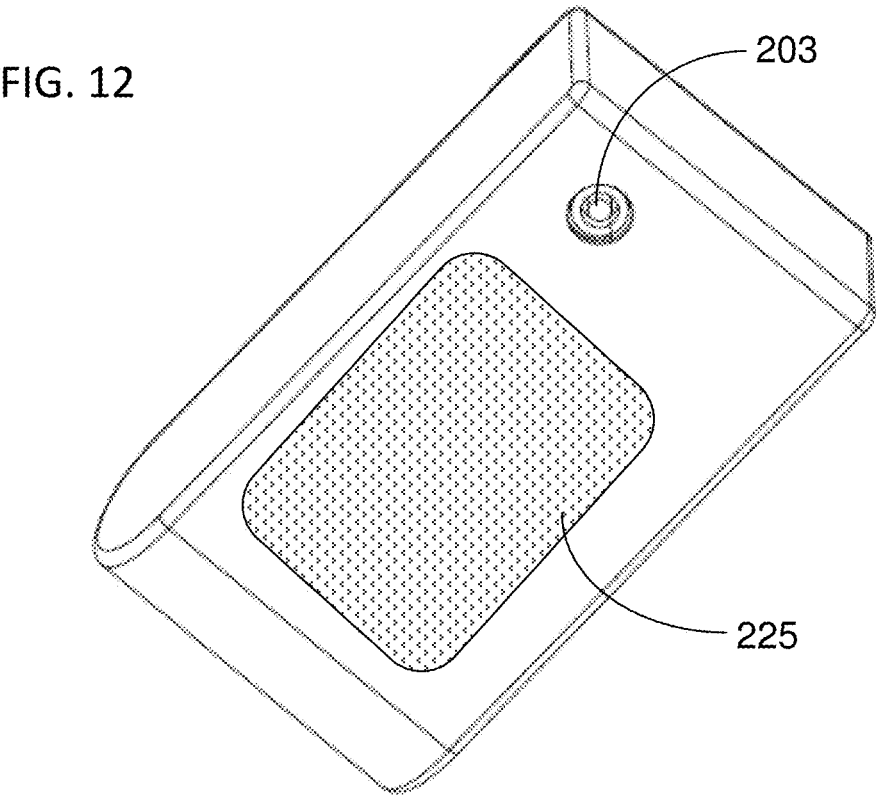
Figure 13:
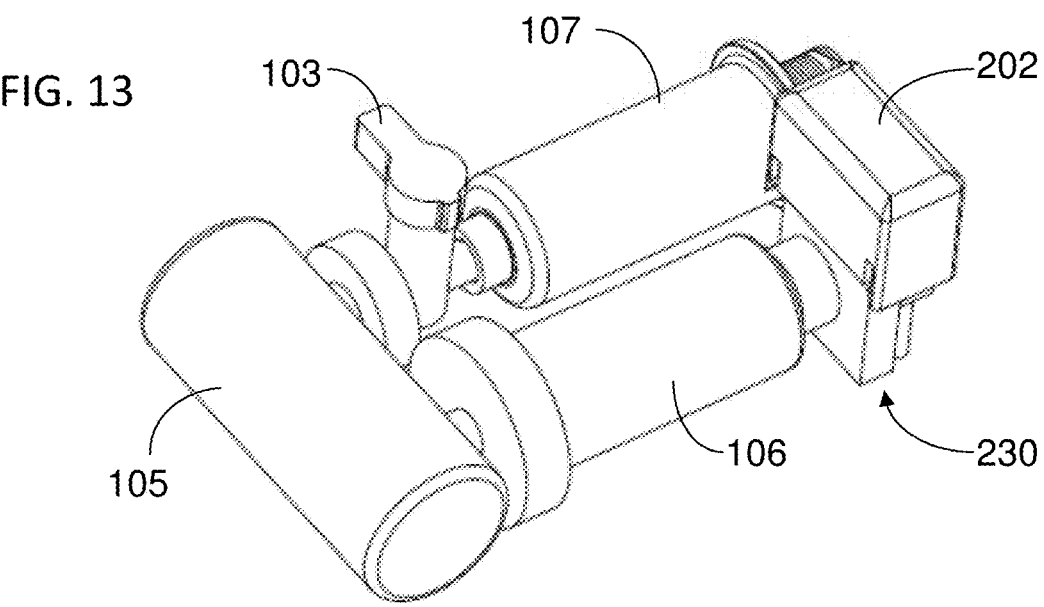
FIG. 13 is a perspective view of the internal components of the first alternative infusion device assembly according to the invention.
Figure 14:
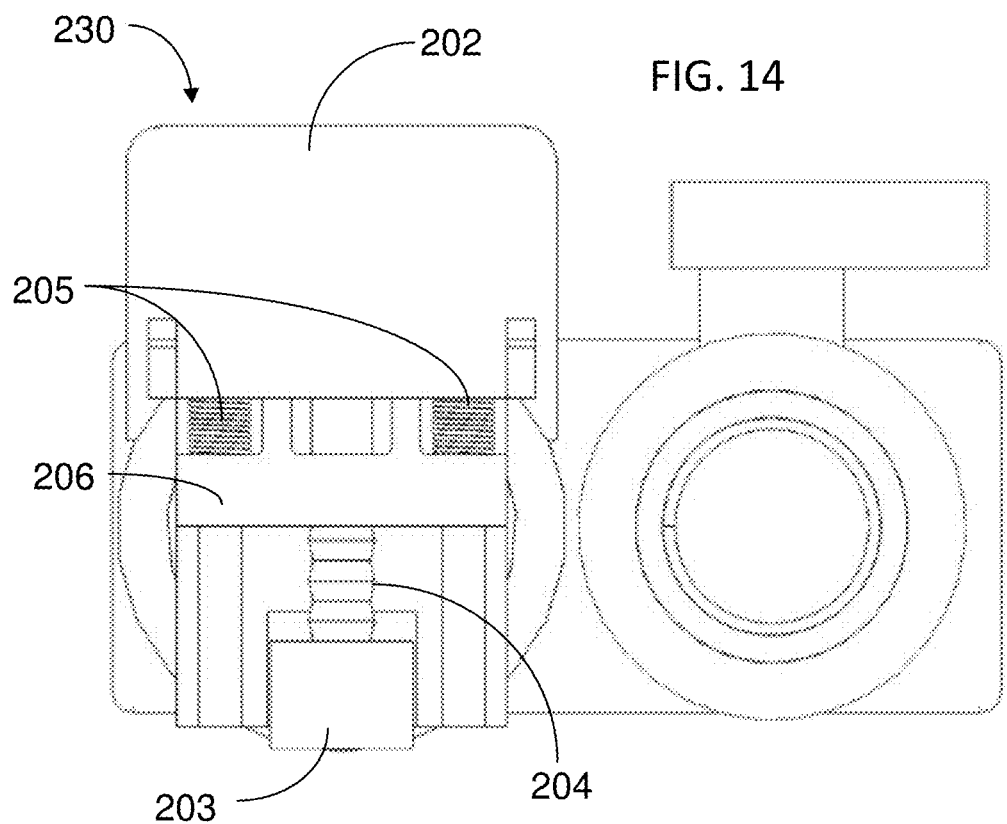
FIG. 14 shows a view of the needle insertion mechanism of the first alternative infusion device assembly according to the invention.
Figure 15:
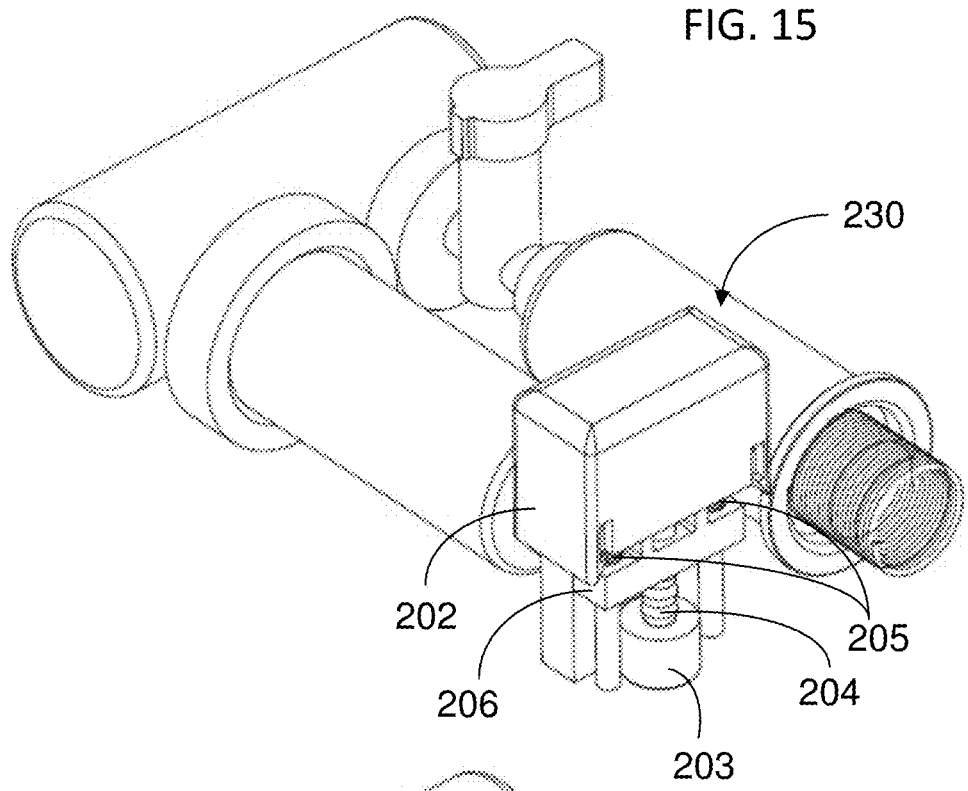
FIG. 15 and FIG. 16 show perspective views of the needle insertion mechanism of the first alternative infusion device assembly according to the invention.
Figure 16:
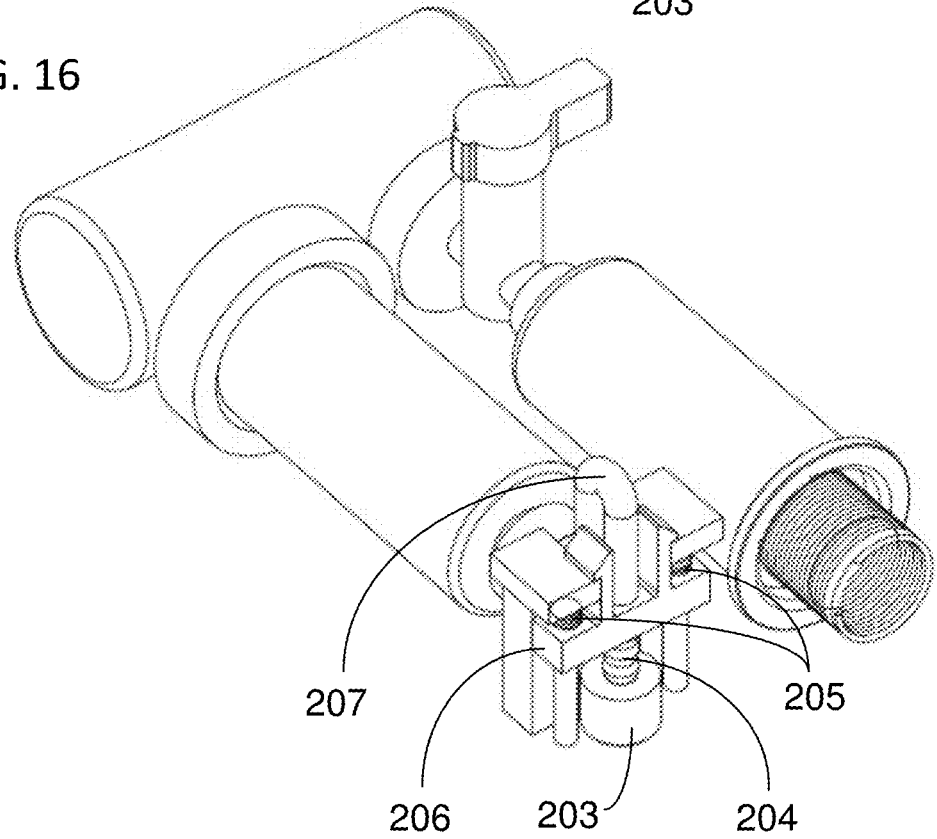
Figure 17:
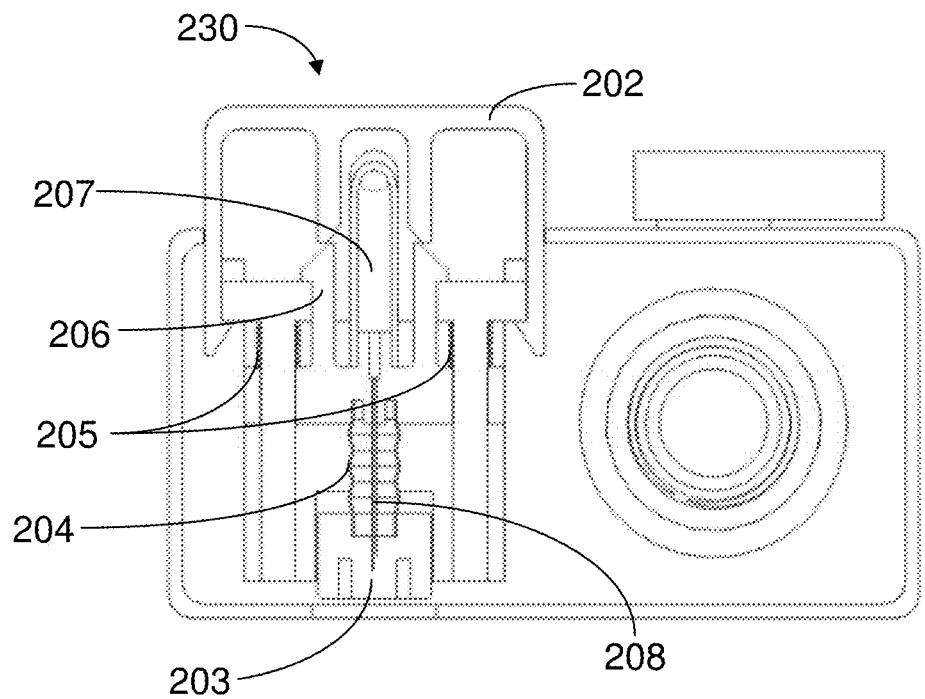
FIG. 17, FIG. 18, FIG. 19 and FIG. 20 show cross-sectional views of the needle insertion mechanism of the first alternative infusion device assembly according to the invention.
Figure 18:
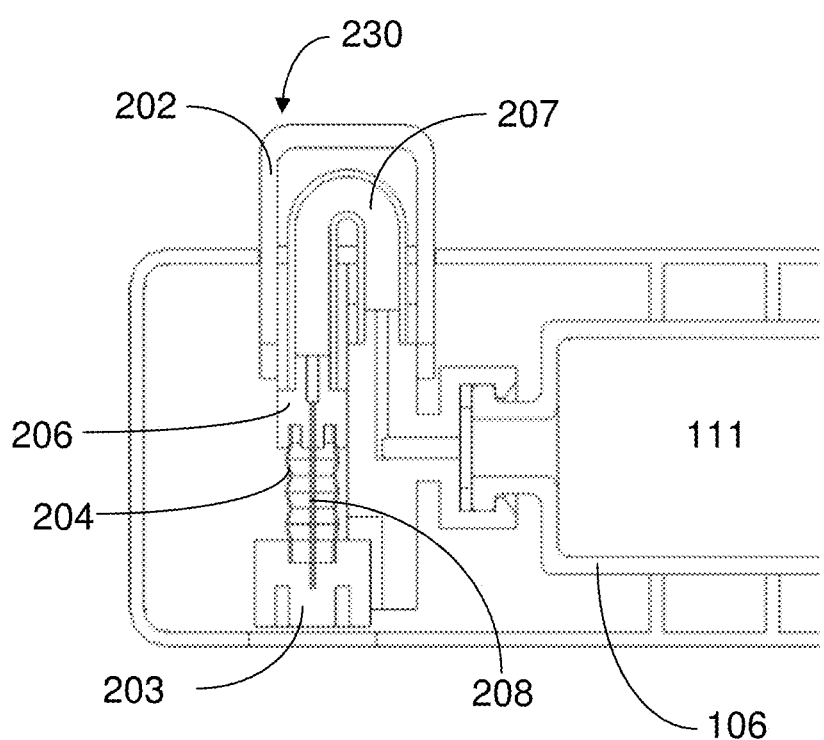
Figure 19:
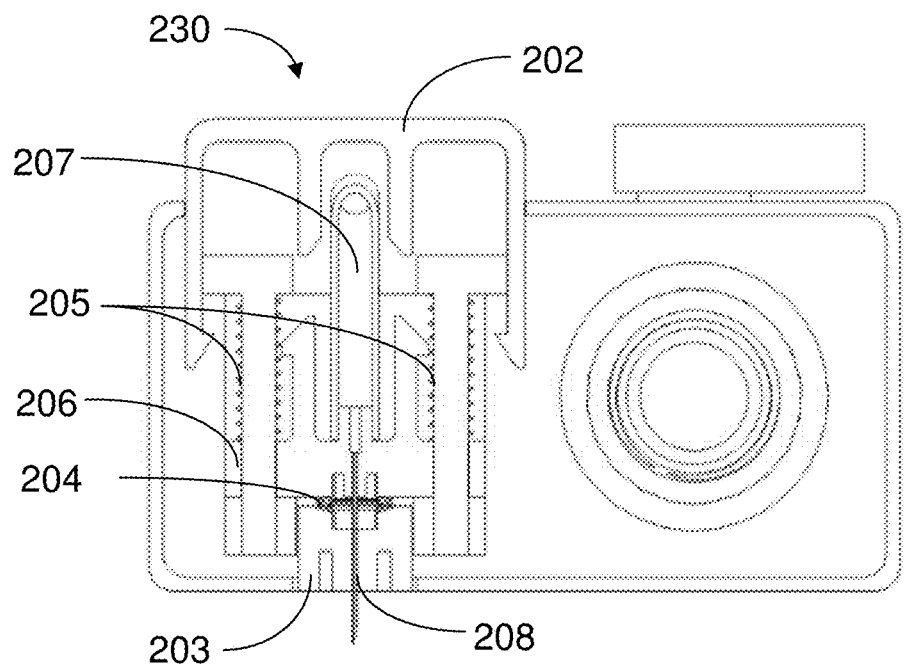
Figure 20:
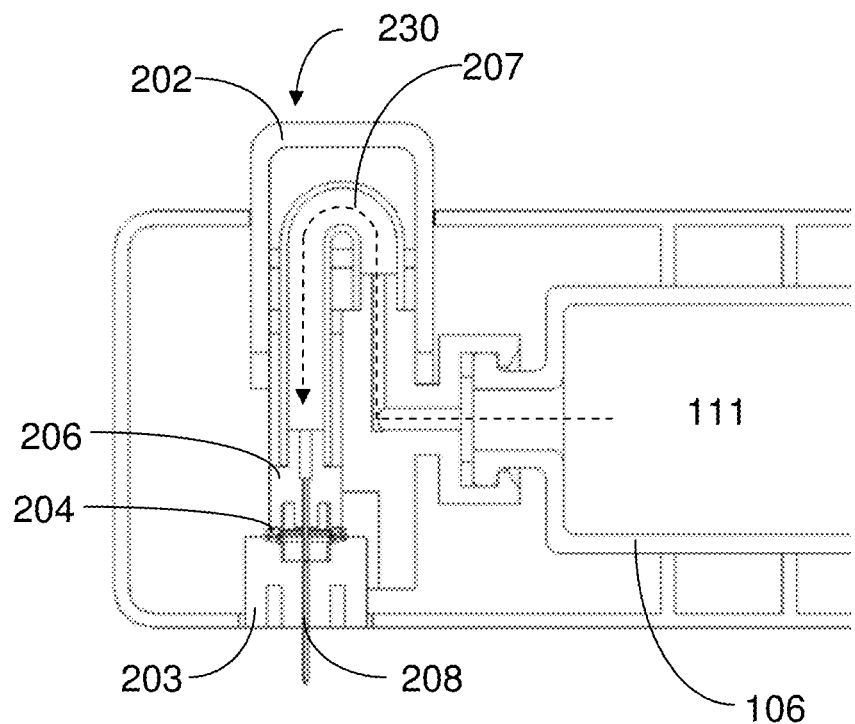
Figure 21:
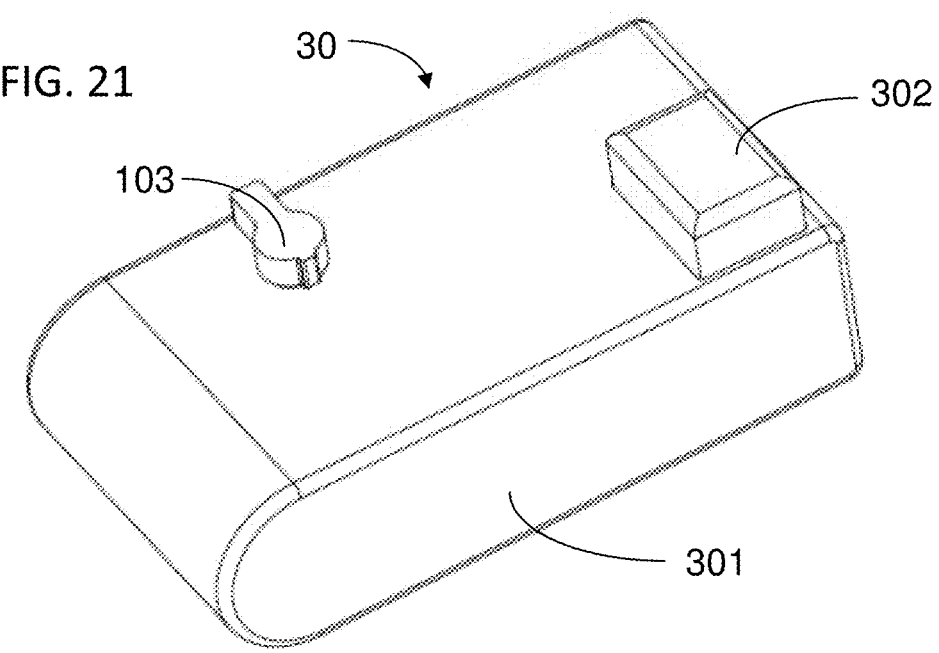
FIG. 21 and FIG. 22 are perspective views of the second alternative infusion alternative device assembly according to the invention.

FIGS. 11-20 illustrate the construction and function mechanism of the first alternative infusion device assembly 20 according to the invention. With reference to FIGS. 11, 12 and 13, the infusion device assembly 20 has the same osmotic pressure based medication delivery mechanism as used in the infusion device assembly 10. Major components of the infusion device assembly 20 including a housing 201, the fluid control switch 103, the pre-filled medication container 106, the water container 107, the osmotic chamber 105 and a needle insertion mechanism 230. With reference to FIG. 12, an adhesive layer 225 is used to attach the infusion device assembly 20 at the infusion site. With reference to FIGS. 13-20, the needle insertion mechanism 230 has major components including a push cap 202, a flexible connection tube 207, a compressible tube 204, a needle driver 206, needle driving springs 205, a pierceable elastomeric septum 203, and an infusion needle 208. The flexible connection tube 207, the needle driver 206, the compressible tube 204 and the pierceable elastomeric septum 203 keep the sterility for the infusion needle 208 and the liquid medication 111. With reference to FIGS. 17-20, at the beginning of the medication infusion, user pushes down the push cap 202, the downward movement of the push cap 202 causes releasing of the needle driver 206. Then, the needle driving springs 205 push the needle driver 206 and the infusion needle 208 downward. During the downward movement of the infusion needle 208, the distal end of the infusion needle 208 pierces through the pierceable septum 203 and insert into body site for medication infusion. The dash line with arrow in FIG. 20 indicates the fluid path of the liquid medication 111 during medication infusion.

Figure 22:
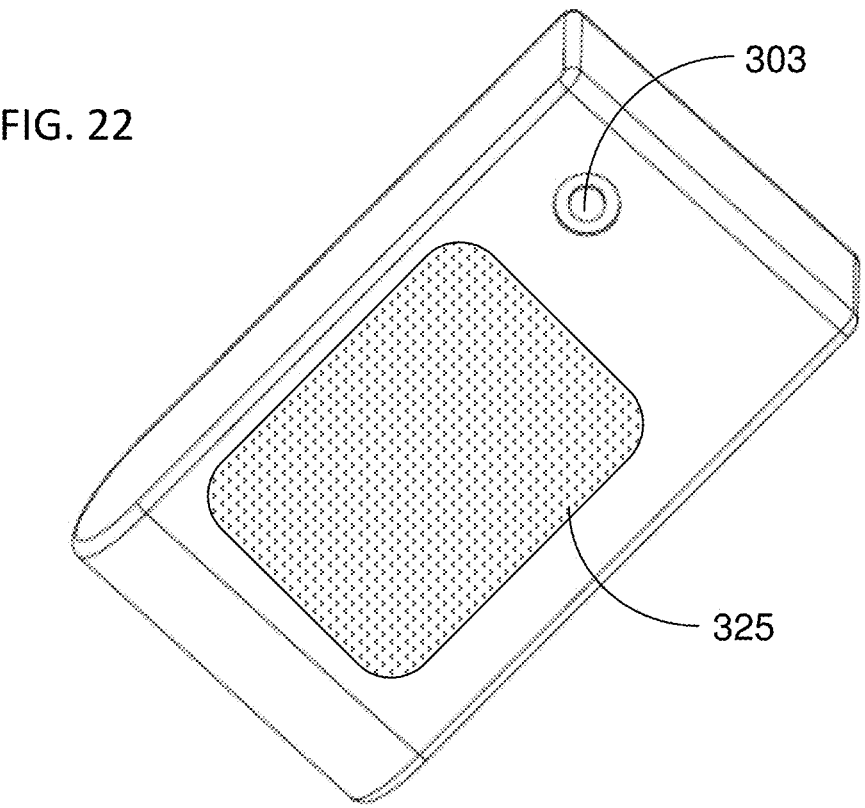
Figure 23:
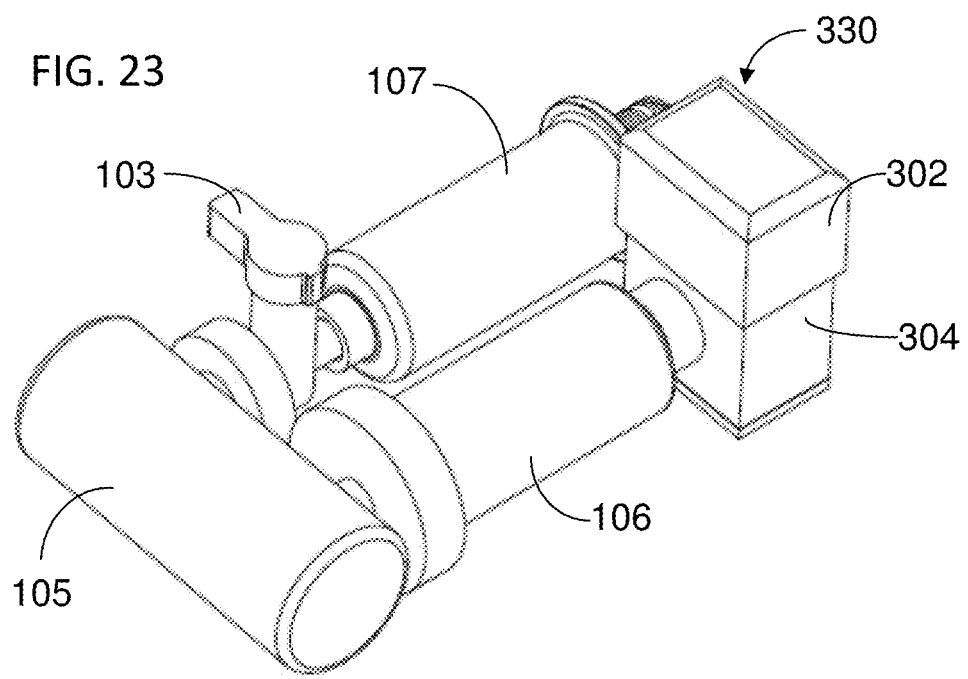
FIG. 23 and FIG. 24 are perspective views of the internal components of the second alternative infusion device assembly according to the invention.
Figure 24:
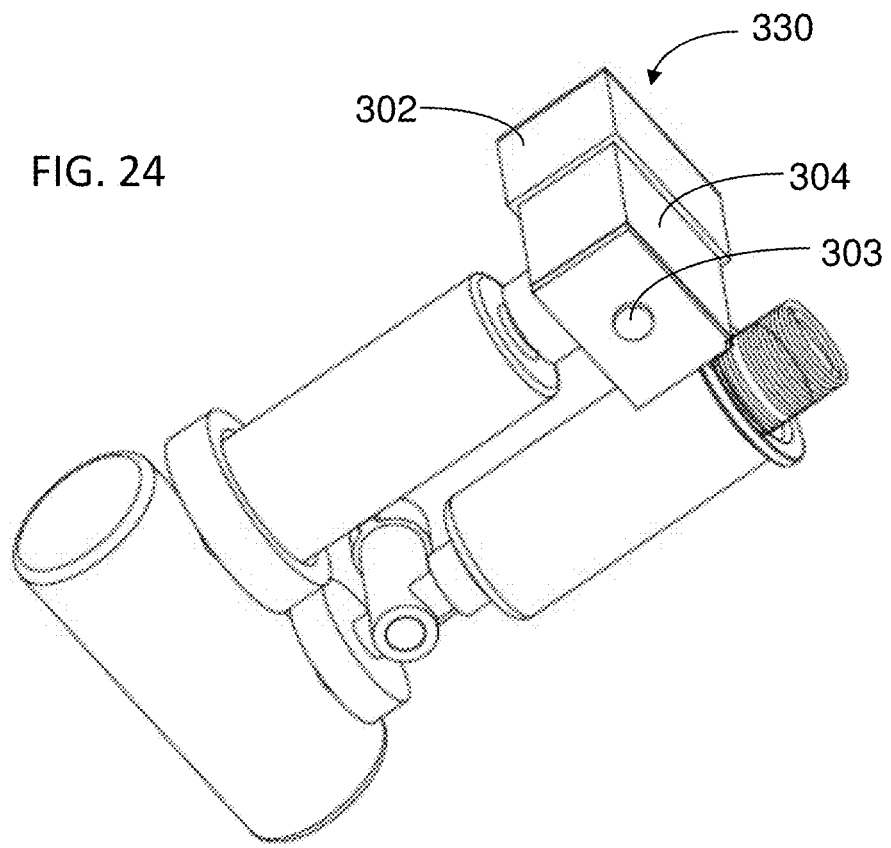
Figure 25:
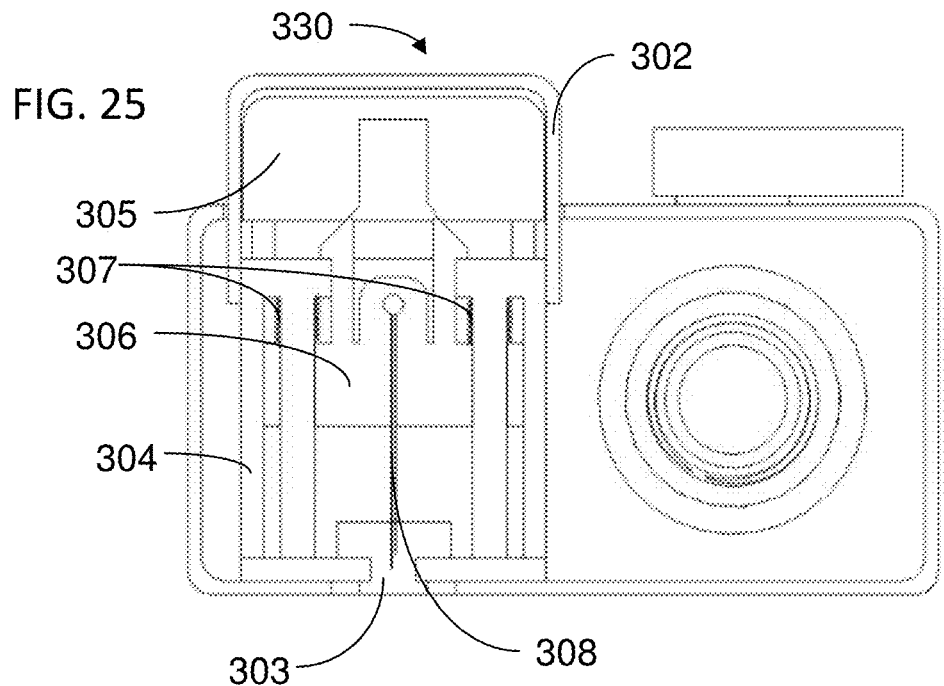
Figure 26:
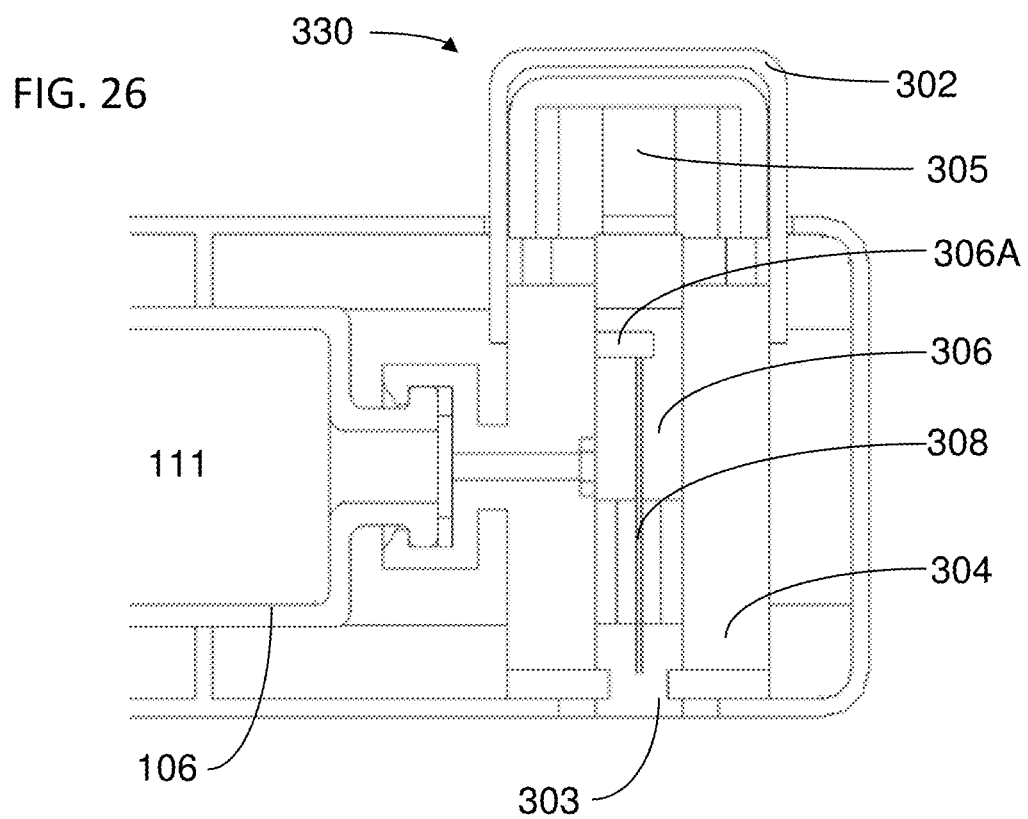

FIGS. 21-28 illustrate the construction and function mechanism of the second alternative infusion device assembly 30 according to the invention. With reference to FIGS. 21, 22, 23 and 24, the infusion device assembly 30 has the same osmotic pressure based medication delivery mechanism as used in the infusion device assembly 10. Major components of the infusion device assembly 30 including a housing 301, the fluid control switch 103, the pre-filled medication container 106, the water container 107, the osmotic chamber 105 and a needle insertion mechanism 330. With reference to FIG. 22, an adhesive layer 325 is used to attach the infusion device assembly 30 at the infusion site. With reference to FIGS. 23-28, the needle insertion mechanism 330 has major components including a flexible protection cap 302, a needle housing 304, an activation button 305, a needle driver 306, needle driving springs 307, a pierceable elastomeric septum 303, and an infusion needle 308. The flexible protection cap 302, the needle housing 304 and the pierceable elastomeric septum 303 keep the sterility for the infusion needle 308 and the liquid medication 111. With reference to FIGS. 25-28, at the beginning of the medication infusion, user pushes down the flexible protection cap 302 and the activation button 305, the downward movement of the activation button 305 causes releasing of the needle driver 306. Then, the needle driving springs 307 push the needle driver 306 and the infusion needle 308 downward. During the downward movement of the needle driver 306 and infusion needle 308, a side opening feature 306A on the needle driver 306 aligns with the channel connecting to the medication container 106, so that the liquid medication 111 can flow through the side opening feature 306A. Also during the downward movement of the infusion needle 308, the distal end of the infusion needle 308 pierces through the pierceable septum 303 and insert into body site for medication infusion.

Figure 29:
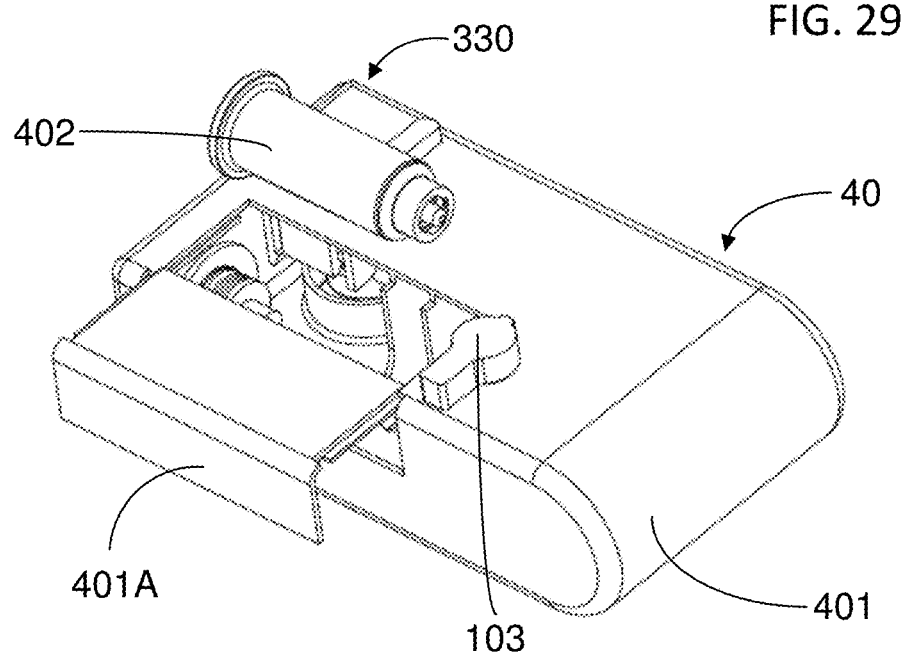
FIG. 29 is a perspective view of the third alternative infusion device assembly according to the invention.
Figure 30:
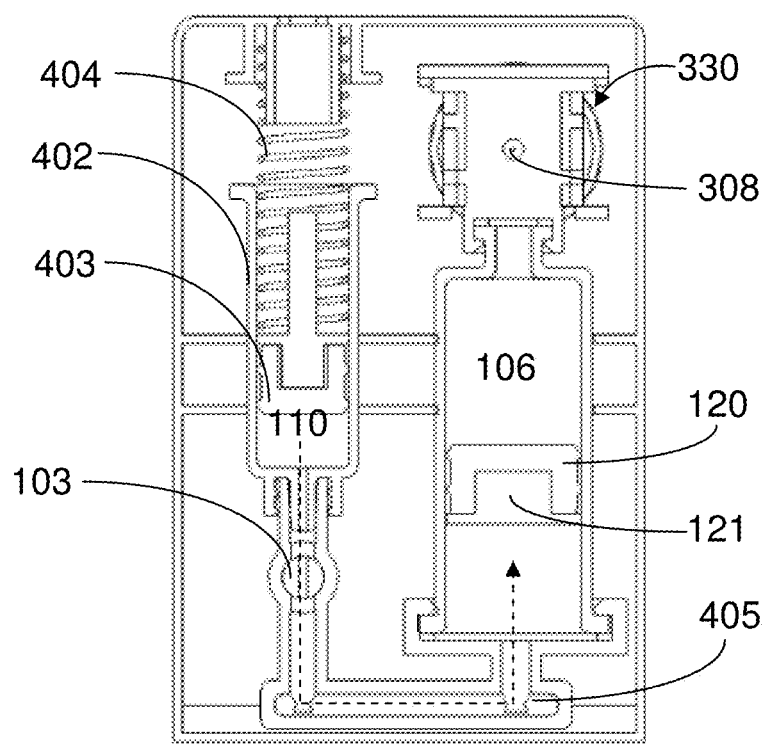
FIG. 30 is a cross-sectional view of the third alternative infusion device assembly according to the invention.

FIGS. 29-30 illustrate the construction and function mechanism of the third alternative infusion device assembly 40 according to the invention. The infusion device assembly 40 has the same needle insertion mechanism 330 as used in the infusion device assembly 30. Major components of the infusion device assembly 40 including a housing 401, the fluid control switch 103, the pre-filled medication container 106, a water container 402, a connecting channel 405 and the needle insertion mechanism 330. With reference to FIG. 30, when the fluid control switch 103 is turned at "on" position, the water 110, pushed by a movable piston 403 and a compression spring 404, flows into the connecting channel 405. Then, the water 110 pushes the rigid plate 121 and the movable piston 120 up, due to hydraulic pressure. Consequently, the liquid medication 111 is pushed out of the medication container 106. The cylindrical inner diameter of the water container 402 may be smaller than the cylindrical inner diameter of the medication container 106. As the result, less amount of mechanical force is required for the compression spring 404 to drive the movable pistons 403 and 120 for medication infusion. Meantime, the amount of water filled in the water container 402 can be adjusted for desired delivery dose. Therefore, the infusion device assembly 40 can enable variable dosing.

Figure 31:
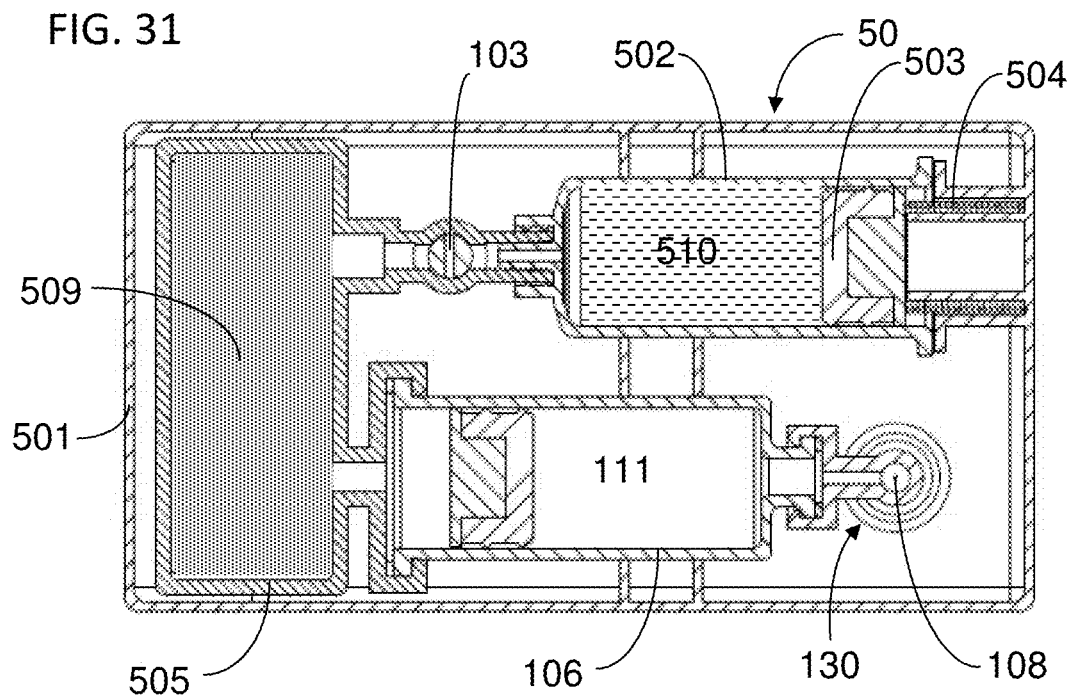
FIG. 31 is a cross-sectional view of the fourth alternative infusion device assembly according to the invention.

FIG. 31 illustrates the construction and function mechanism of the fourth alternative infusion device assembly 50 according to the invention. The infusion device assembly 50 has the same needle insertion mechanism 130 used in the infusion device assembly 10. Major components of the infusion device assembly 50 including a housing 501, the fluid control switch 103, the pre-filled medication container 106, a liquid reagent container 502, a solid reagent container 505 and the needle insertion mechanism 130. The liquid reagent container contains liquid reagent, for example, acetic acid aqueous solution. The solid reagent container 505 contains solid reagent, for example, sodium bicarbonate. When the liquid reagent is mixed with the solid reagent, gas is generated. For example, carbon dioxide can be generated by mixing acetic acid with sodium bicarbonate. With reference to FIG. 30, when the fluid control switch 103 is turned at "off" position, liquid reagent 510 is restrained in the liquid reagent container 502. When the fluid control switch 103 is turned at "on" position, the liquid reagent 510, pushed by a movable piston 503 and a compression spring 504, flows into the solid reagent container 505. As the result, gas can be generated when the liquid reagent mixed with the solid reagent. The compression spring 504 keeps the gas pressurized. Then, the gas pressure resulting from the chemical reaction pushes the rigid plate 121 and the movable piston 120 toward right. Consequently, the liquid medication 111 is pushed out of the medication container 106.

Figure 32:
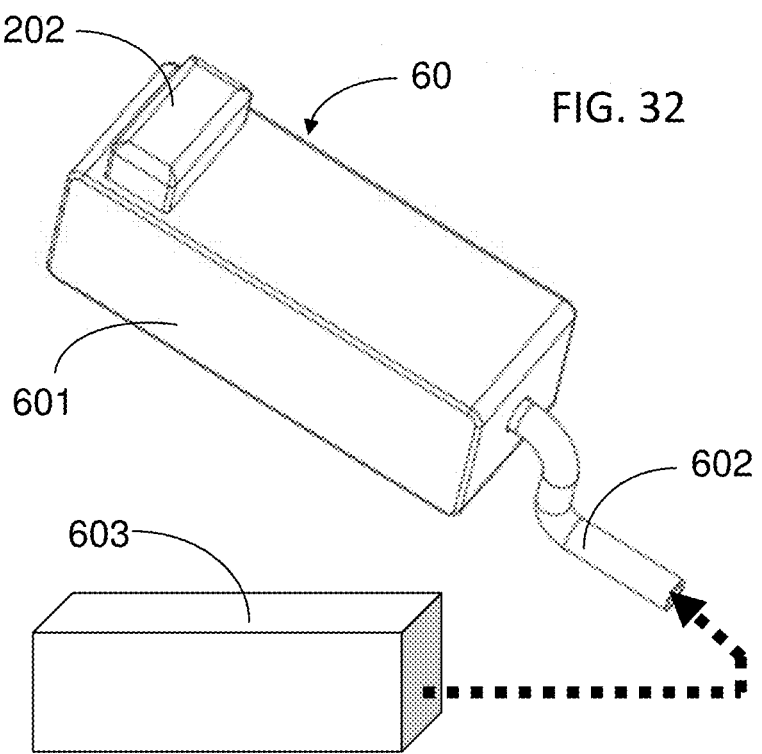
FIG. 32 is a perspective view of the fifth alternative infusion device assembly according to the invention.
Figure 33:
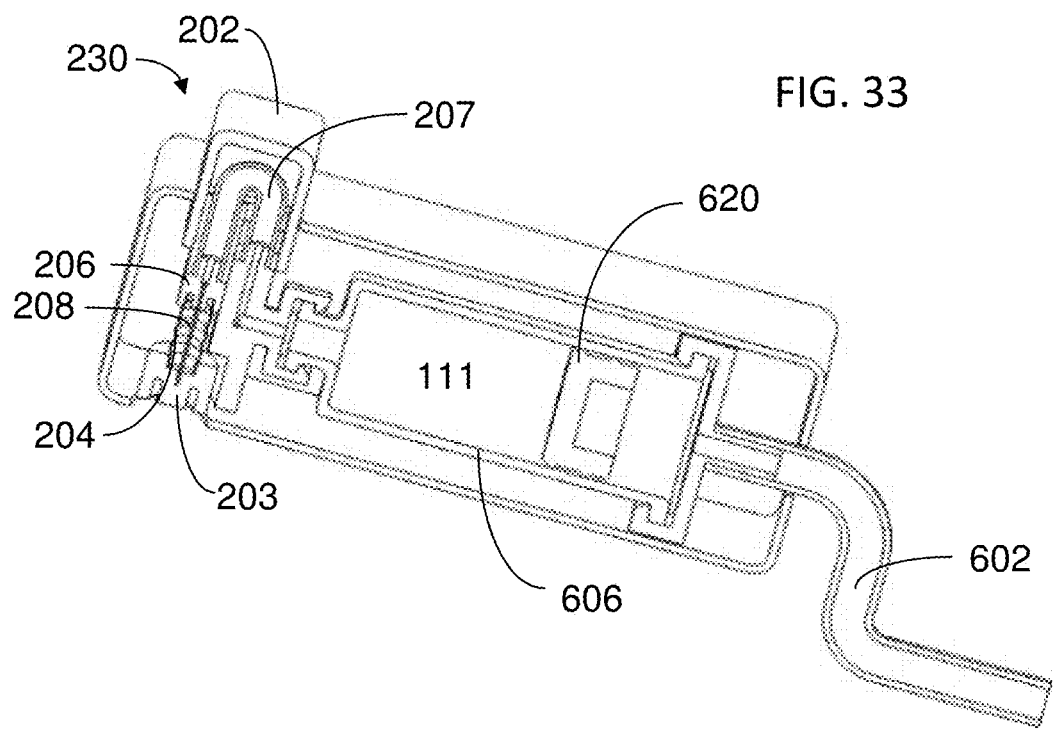
FIG. 33 is a cross-sectional view of the fifth alternative infusion device assembly according to the invention.
Figure 34:
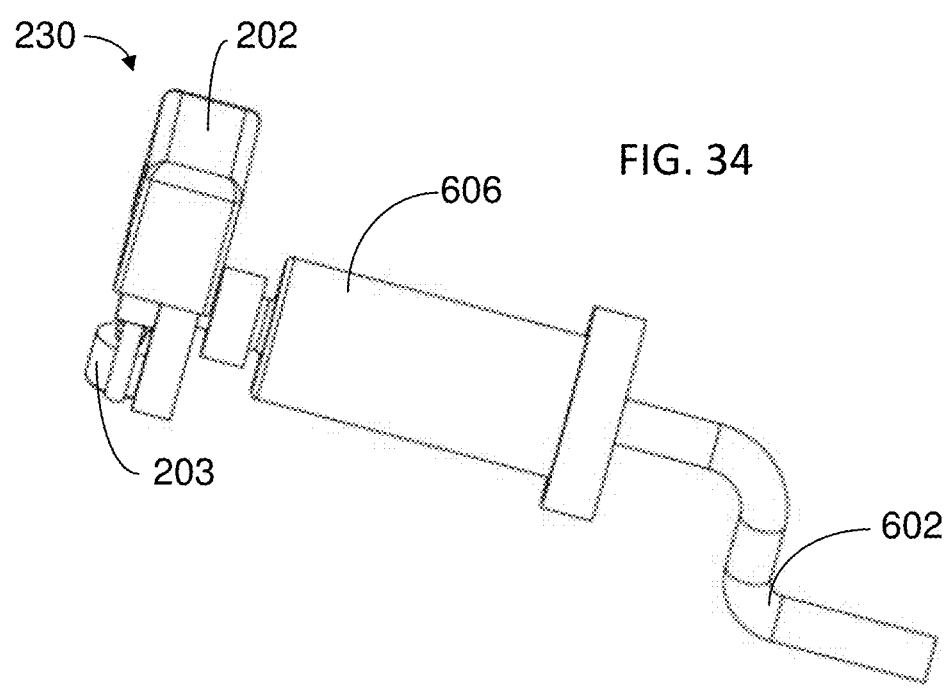
FIG. 34 is a perspective view of the internal components of the fifth alternative infusion device assembly according to the invention.
Figure 35:
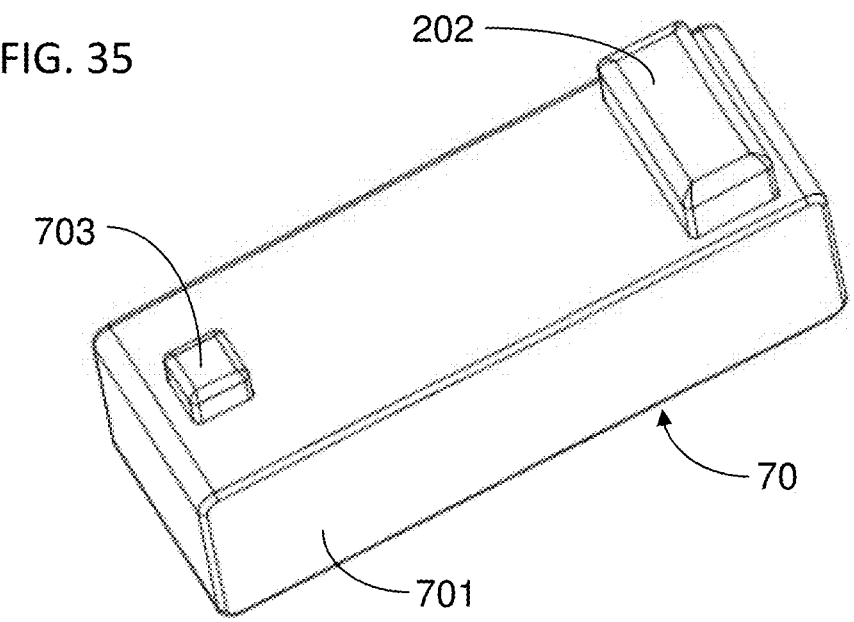
FIG. 35 is a perspective view of the sixth alternative infusion device assembly according to the invention.
Figure 36:
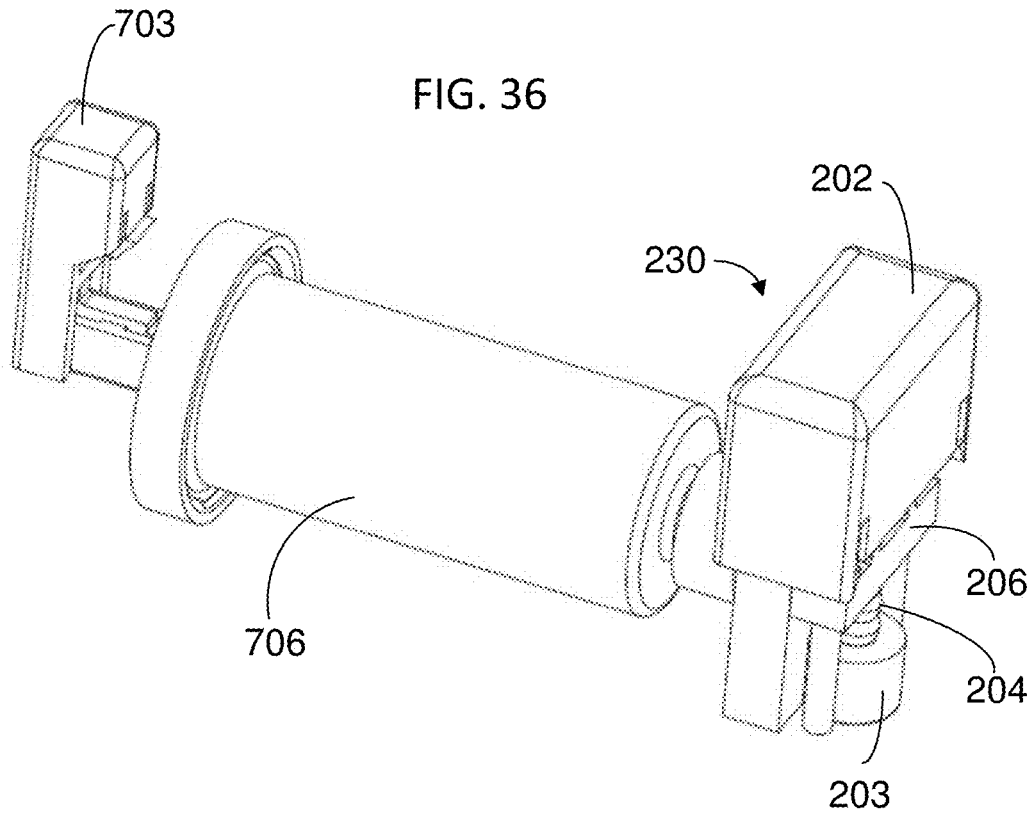
FIG. 36 is a perspective view of the internal components of the sixth alternative infusion device assembly according to the invention.

FIGS. 32-34 illustrate the construction and function mechanism of the fifth alternative infusion device assembly 60 according to the invention. The infusion device assembly 60 has the same needle insertion mechanism 230 as used in the infusion device assembly 20. Major components of the infusion device assembly 60 including a housing 601, a pre-filled medication container 606, a connecting tube 602, a gas pump 603 and the needle insertion mechanism 230. The liquid medication 111 is sealed in the medication container 606 by a movable piston 620. With reference to FIGS. 32-34, gas pressure generated by the gas pump 603 pushes the movable piston 620 toward to the needle side of the medication container 606. Consequently, the liquid medication 111 is pushed out of the medication container 606 for infusion.

Figure 37:
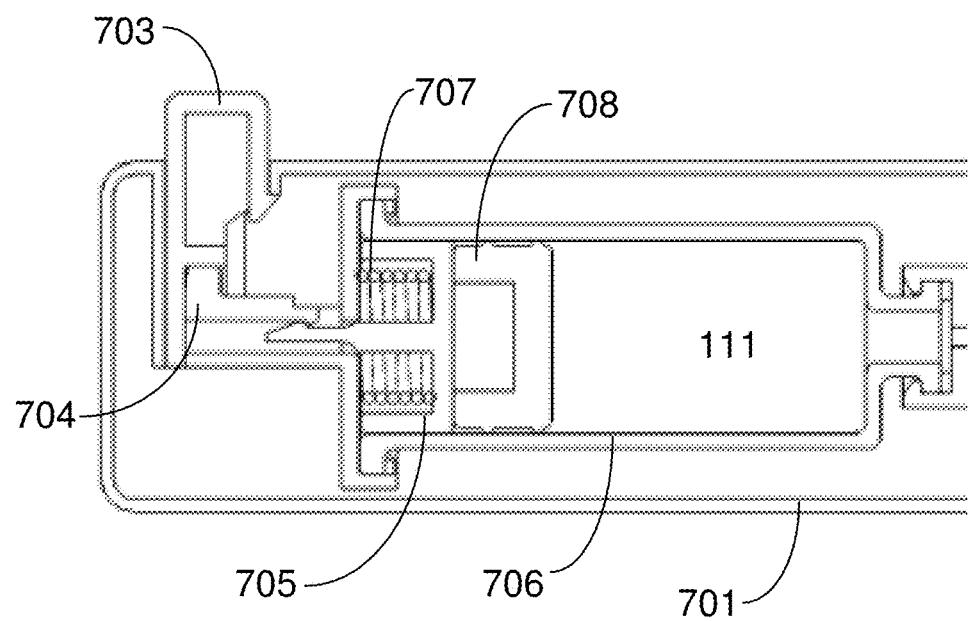
FIG. 37 and FIG. 38 show cross-sectional views of a mechanical spring based medication delivery mechanism of the sixth alternative infusion device assembly according to the invention.
Figure 38:
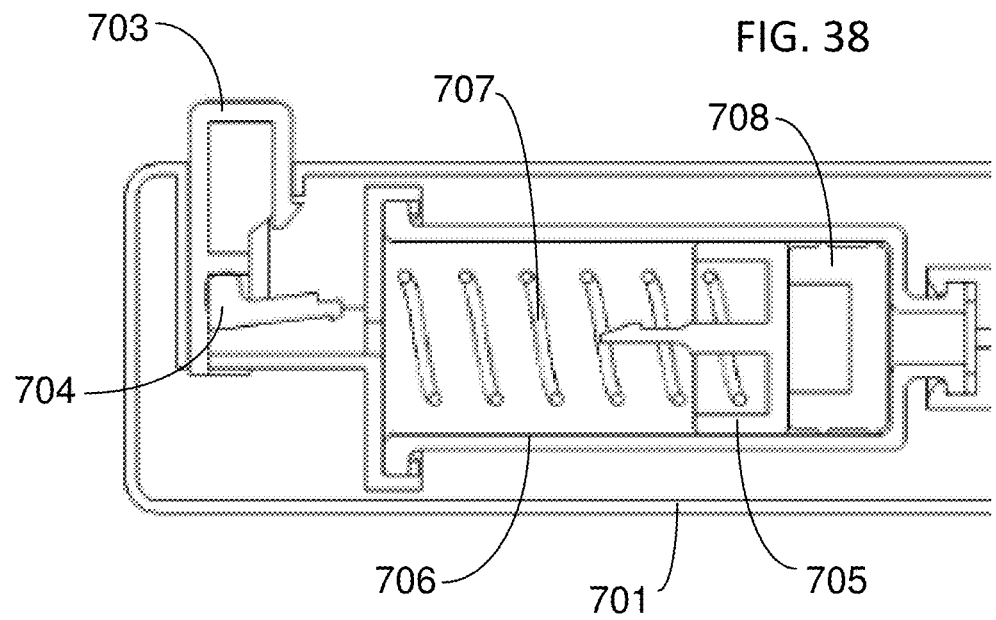
Figure 39:
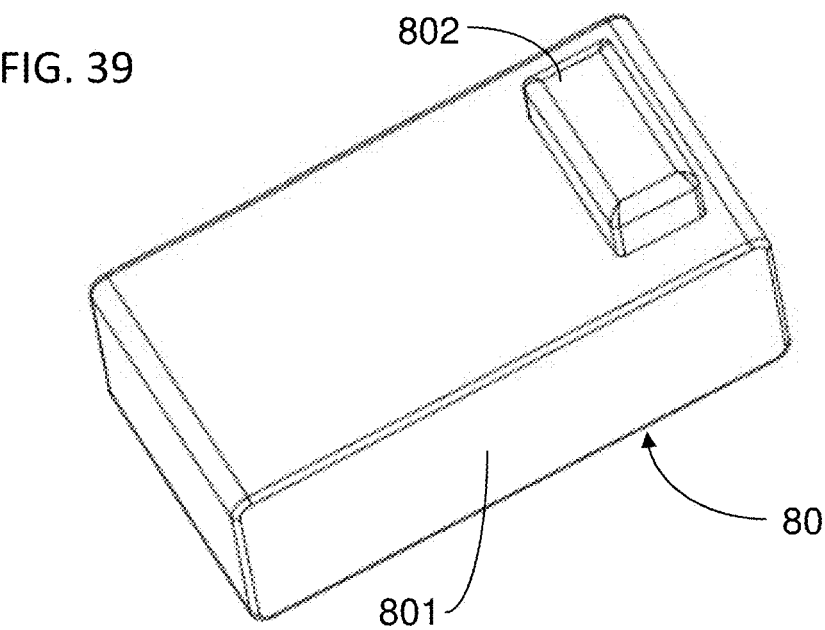
FIG. 39 is a perspective view of the seventh alternative infusion device assembly according to the invention.

FIGS. 35-38 illustrate the construction and function mechanism of the sixth alternative infusion device assembly 70 according to the invention. The infusion device assembly 70 has the same needle insertion mechanism 230 as used in the infusion device assembly 20. Major components of the infusion device assembly 70 including a housing 701, a pre-filled medication container 706, a push button 703, a latch locking feature 704, a piston driver 705, a piston driving spring 707 and the needle insertion mechanism 230. The liquid medication 111 is sealed in the medication container 706 by a movable piston 708. With reference to FIGS. 37 and 38, when user pushes down the push button 703, the downward movement of the push button 703 causes rotation of the latch locking feature 704. Then, the piston driver 705 is released and the piston driving spring 707 pushes the piston driver 705 and the movable piston 708 toward to the needle side of the medication container 706. Consequently, the liquid medication 111 is pushed out of the medication container 706 for infusion.

Figure 40:
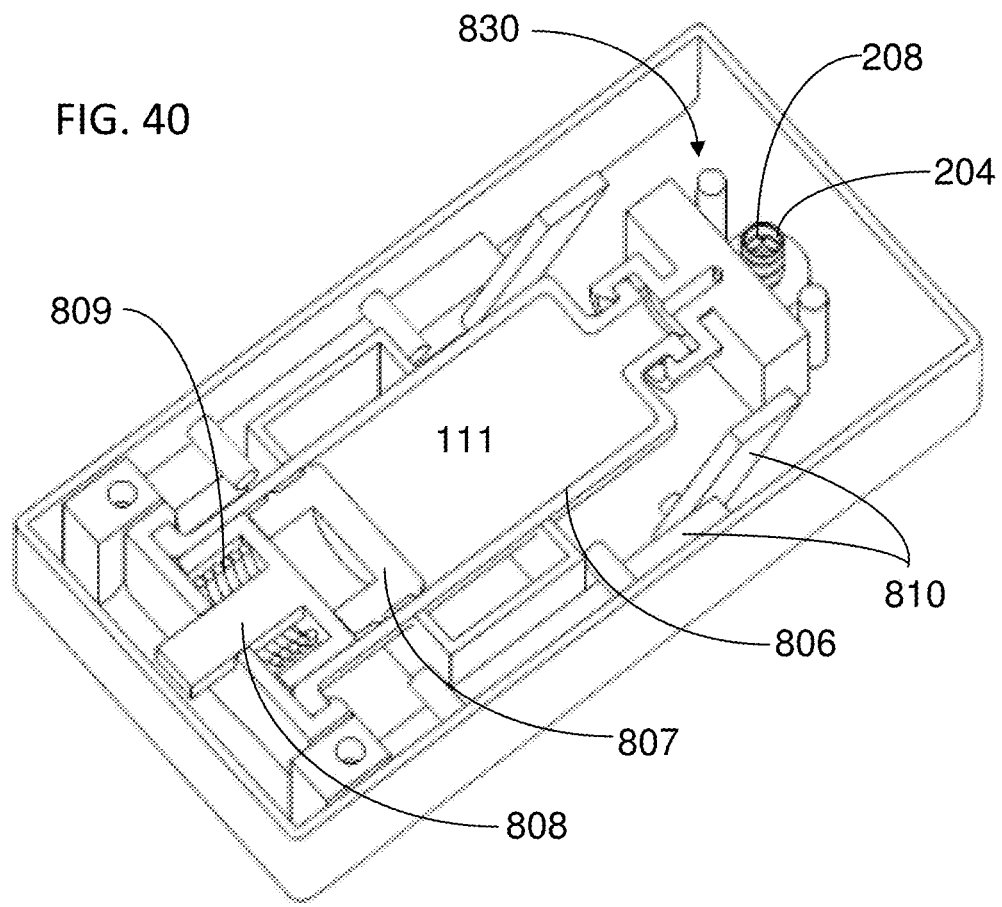
FIG. 40 is a cross-sectional view of the seventh alternative infusion device assembly according to the invention.
Figure 41:
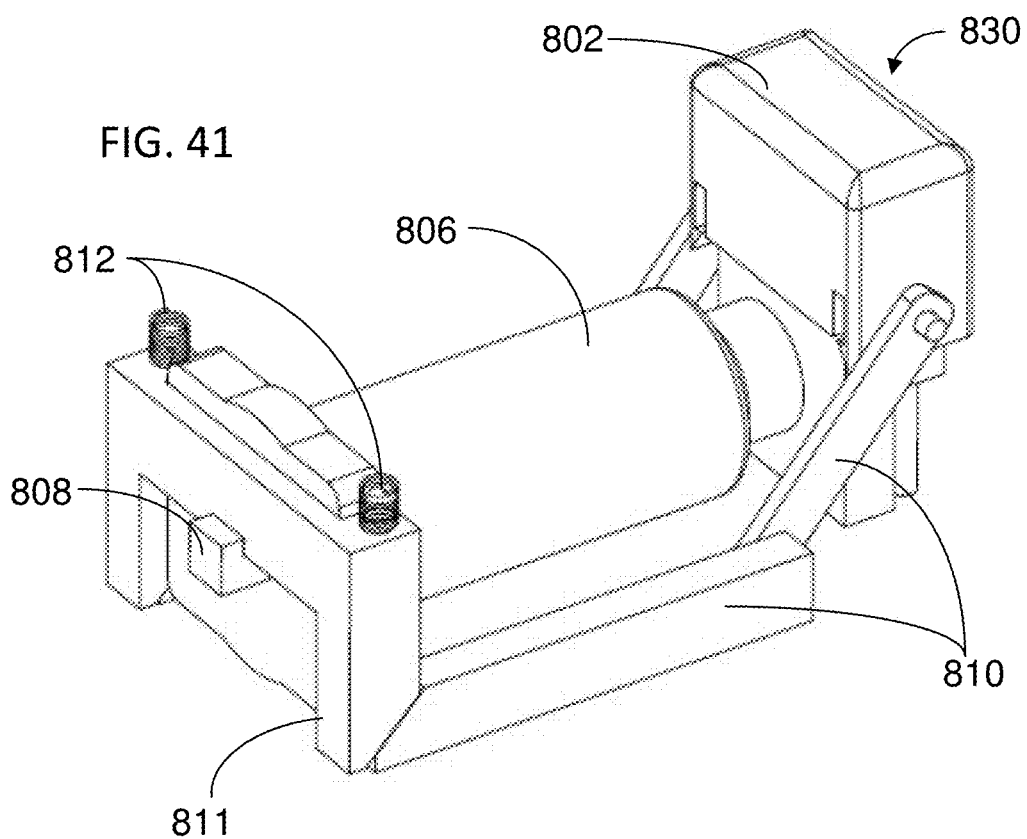
FIG. 41 and FIG. 42 show perspective views of the internal components of the seventh alternative infusion device assembly according to the invention.
Figure 42:
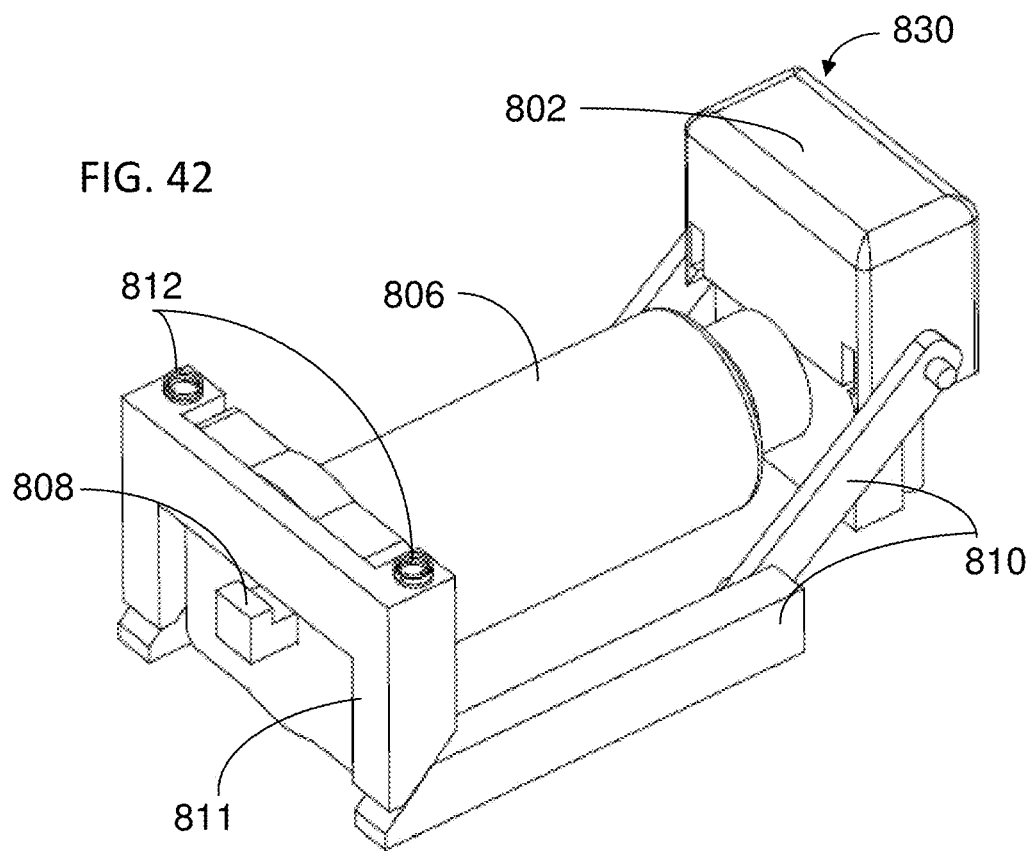
Figure 43:
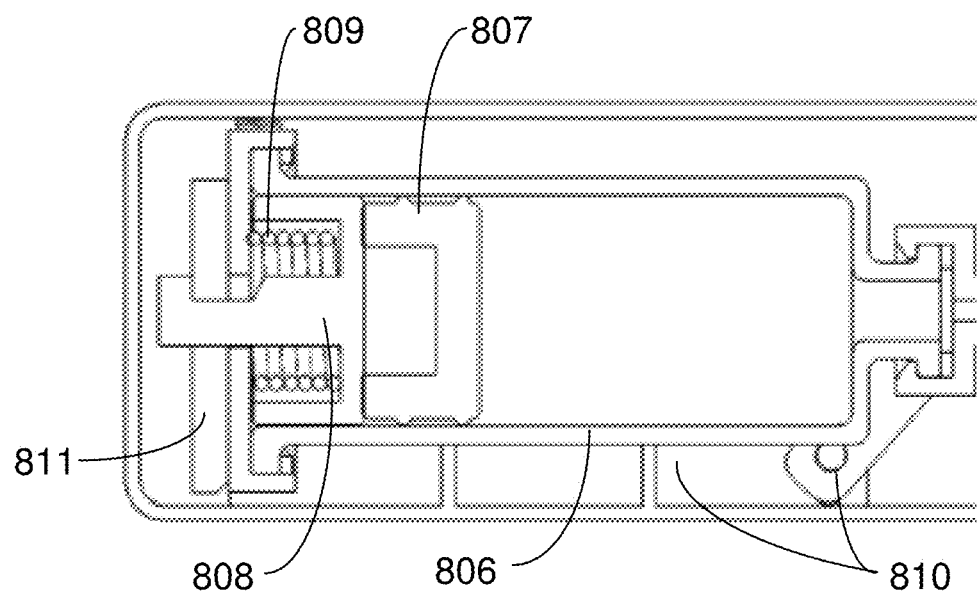
FIG. 43 and FIG. 44 show cross-sectional views of a mechanical spring based medication delivery mechanism of the seventh alternative infusion device assembly according to the invention.
Figure 44:
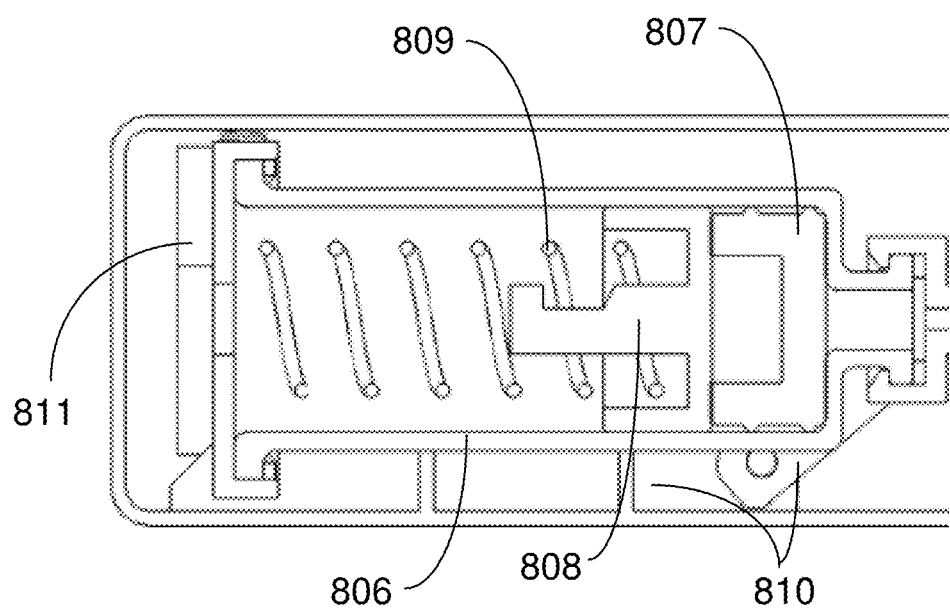
Figure 45:
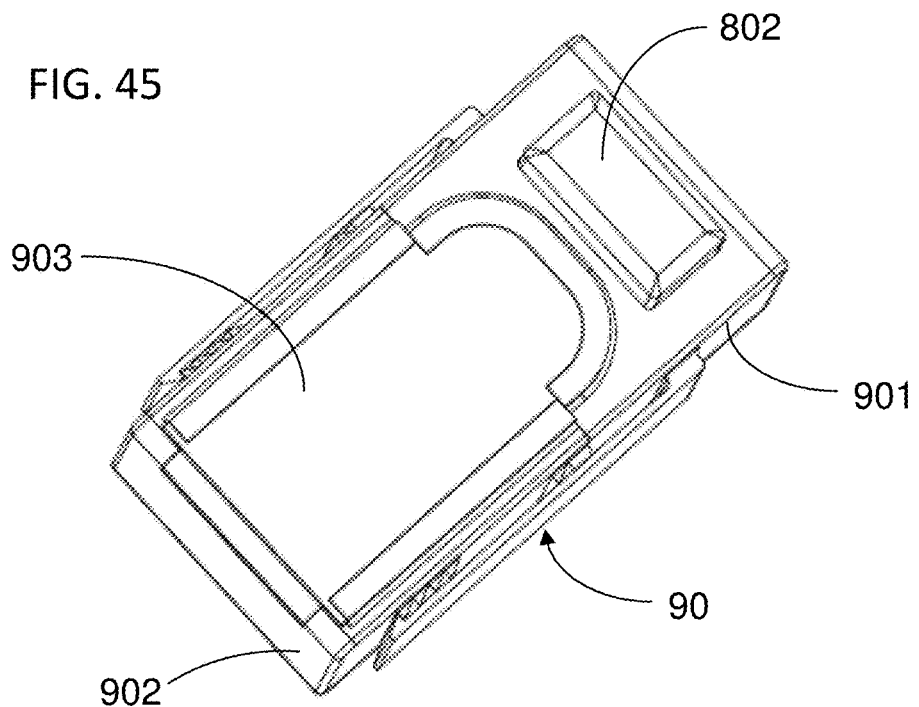
FIG. 45 is a perspective view of the eighth alternative infusion device assembly according to the invention.

FIGS. 39-44 illustrate the construction and function mechanism of the seventh alternative infusion device assembly 80 according to the invention. Major components of the infusion device assembly 80 including a housing 801, a pre-filled medication container 806, a piston driver 808, a piston driving spring 809, a piston driver block 811, piston driver block positioning springs 812, linkages 810 and a needle insertion mechanism 830. The needle insertion mechanism 830 is the same as the needle insertion mechanism 230 used in the infusion device assembly 20, except a modified push cap 802 is used in the infusion device assembly 80. Here, the push cap 802 is engaged with linkages 810. With reference to FIG. 40, the liquid medication 111 is sealed in the medication container 806 by a movable piston 807. With reference to FIGS. 40-44, when user pushes down the push cap 802, the downward movement of the push cap 802 activates the needle insertion. At the same time, the downward movement of the push cap 802 also release the piston driver 808 by raising up the piston driver block 811 through the interaction between the piston driver block 811 and linkages 810. After the piston driver 808 is released, the piston driving spring 809 pushes the piston driver 808 and the movable piston 807 toward to the needle end of the medication container 806. Consequently, the liquid medication 111 is pushed out of the medication container 806 for infusion.

Figure 46:
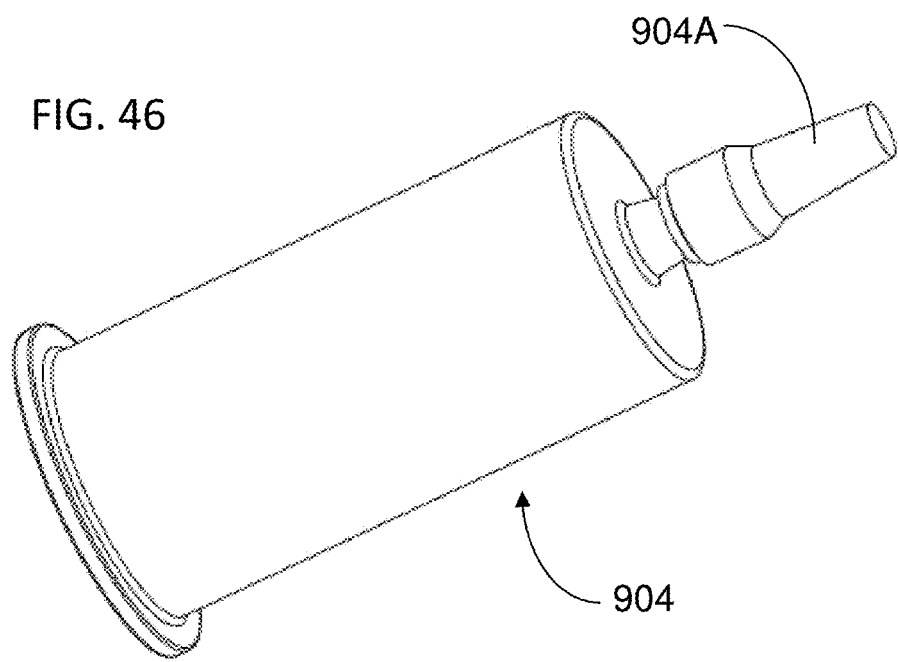
FIG. 46 is a perspective view of a pre-filled syringe used as medication container in the eighth alternative infusion device assembly according to the invention.

FIGS. 45-48 illustrate the construction and function mechanism of the eighth alternative infusion device assembly 90 according to the invention. Major components of the infusion device assembly 90 including an upper housing 901, a lower housing 902, a top sliding door 903, a pre-filled syringe 904 as medication container, a piston driver 908, a piston driving spring 909, a piston driver block 911, linkages 910 and a needle insertion mechanism 930. The needle insertion mechanism 930 is the same as the needle insertion mechanism 830 used in the infusion device assembly 80, except a modified interface design between the pre-filled syringe 904 and the needle insertion mechanism 930. With reference to FIG. 48, a pierceable elastomeric septum 905 is used at the interface between the pre-filled syringe 904 and the needle insertion mechanism 930. With reference to FIGS. 46-48, to assemble the pre-filled syringe 904 into the infusion device assembly 90, a needle shield 904A is first removed. Then, align a needle 904B on the pre-filled syringe 904 with the needle insertion mechanism 930 and close the upper housing 901 and the lower housing 902. When the upper housing 901 and the lower housing 902 are closed, the needle 904B pierces through the pierceable elastomeric septum 905 so that the liquid medication 111 can flow from the pre-filled syringe 904 into the fluid path in the needle insertion mechanism 930.

Figure 49:
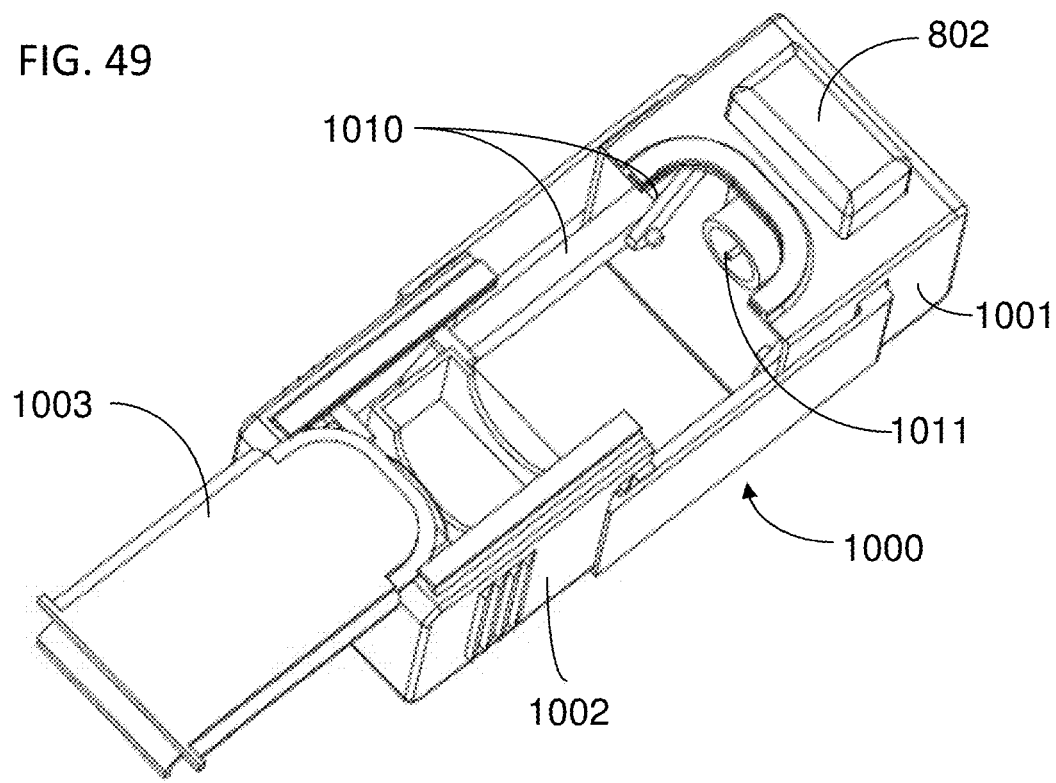
FIG. 49 is a perspective view of the ninth alternative infusion device assembly before being assembled with a pre-filled cartridge, according to the invention.
Figure 50:
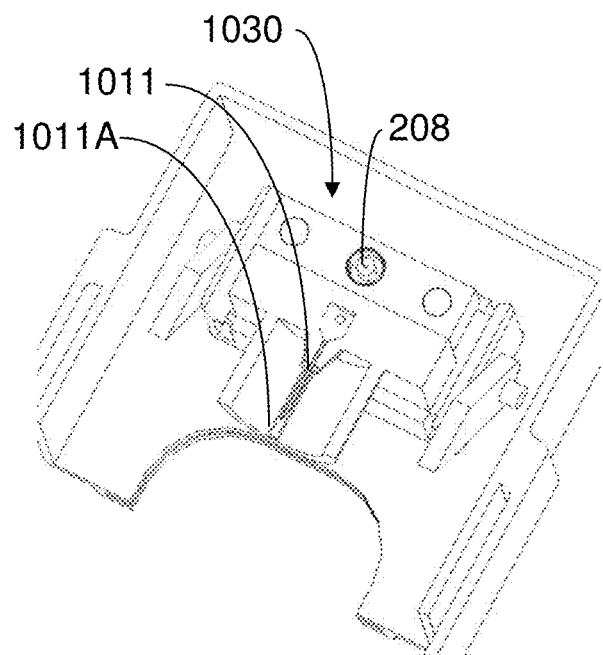
FIG. 50 and FIG. 51 are cross-sectional views of the interface design between the pre-filled cartridge and other components in the ninth alternative infusion device assembly according to the invention.
Figure 51:
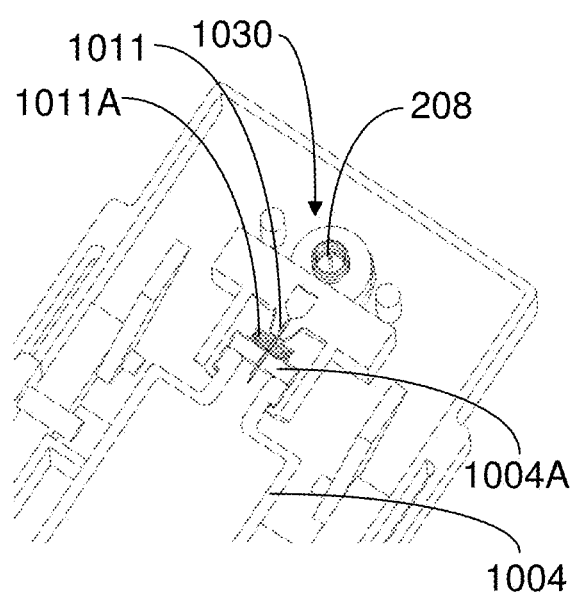
Figure 52:
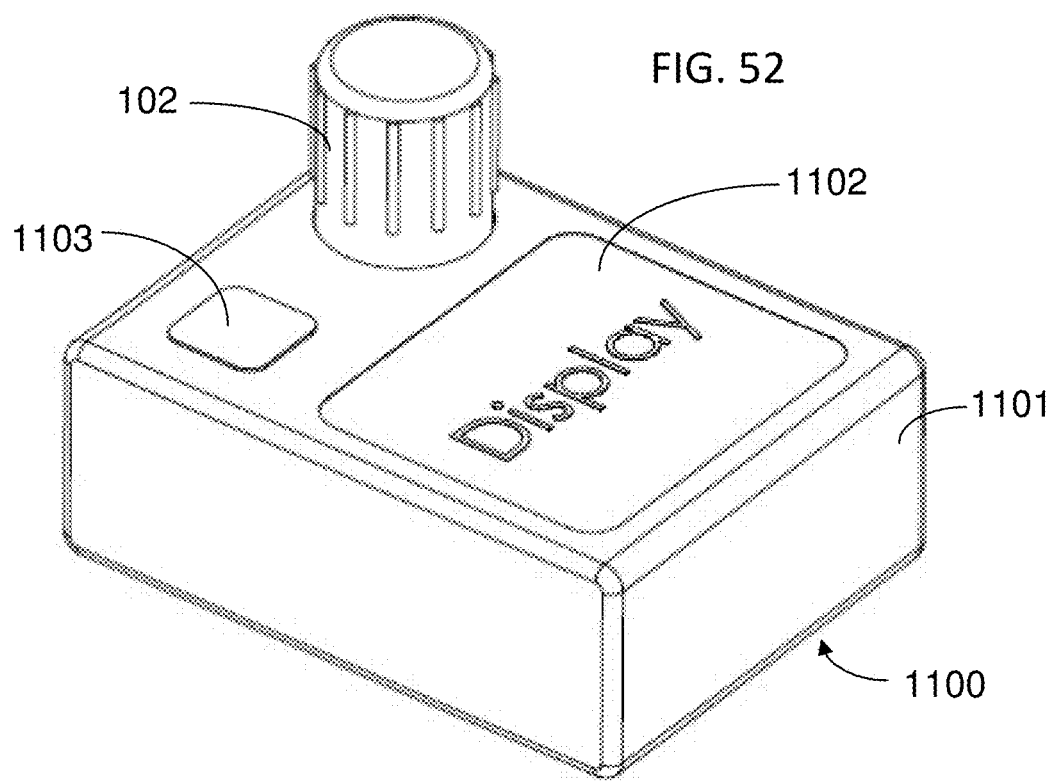
FIG. 52 is a perspective view of the tenth alternative infusion device assembly according to the invention.

FIGS. 49-51 illustrate the construction and function mechanism of the ninth alternative infusion device assembly 1000 according to the invention. Major components of the infusion device assembly 1000 including an upper housing 1001, a lower housing 1002, a top sliding door 1003, a pre-filled cartridge 1004 as medication container, a piston driver 1008, a piston driving spring 1009, a piston driver block 1012, linkages 1010 and a needle insertion mechanism 1030. The piston driver 1008, the piston driving spring 1009 and the piston driver block 1012 (not shown) in the infusion device assembly 1000 have the same designs as the corresponding components in the infusion device assembly 90. The needle insertion mechanism 1030 is the same as the needle insertion mechanism 930 used in the infusion device assembly 90, except a modified interface design for the pre-filled cartridge 1004 as medication container to be assembled with the needle insertion mechanism 1030. With reference to FIGS. 50 and 51, a connecting needle 1011 together with a pierceable elastomeric needle sheath 1011A is used at the interface between the pre-filled cartridge 1004 and the needle insertion mechanism 1030. The pierceable elastomeric needle sheath 1011A keeps the sterility of the connecting needle 1011. When the pre-filled cartridge is assembled in the infusion device assembly 1000, the connecting needle 1011 pierces through the pierceable elastomeric needle sheath 1011A and an elastomeric seal septum 1004A on the pre-filled cartridge 1004 so that the liquid medication 111 can flow from the pre-filled cartridge 1004 into the fluid path in the needle insertion mechanism 1030.

Regarding to the needle insertion mechanism 930 in the infusion device assembly 90 and the needle insertion mechanism 1030 in the infusion device assembly 1000, the infusion needle 208 does not need to be embedded in the pierceable elastomeric septum 203, before the fluid path is established between the medication container (either pre-filled syringe or pre-filled cartridge) and other components in the infusion device assembly 90 and 1000.

Figure 53:
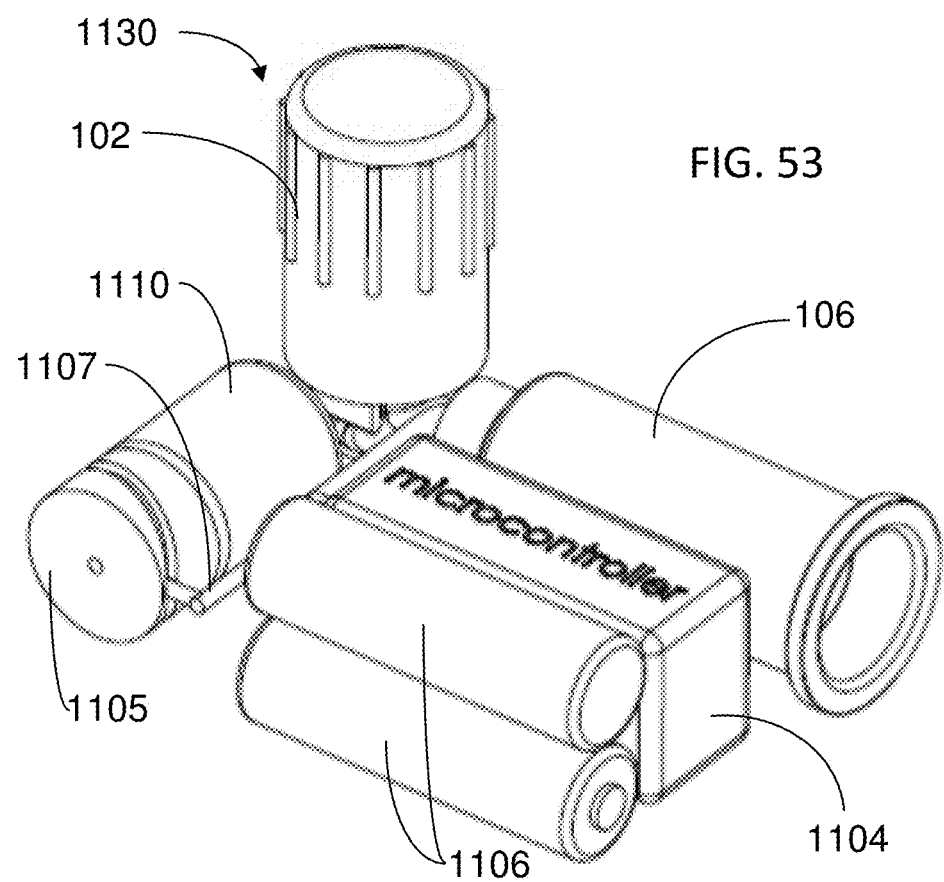
FIG. 53 shows a perspective view of the internal components of the tenth alternative infusion device assembly according to the invention.
Figure 54:
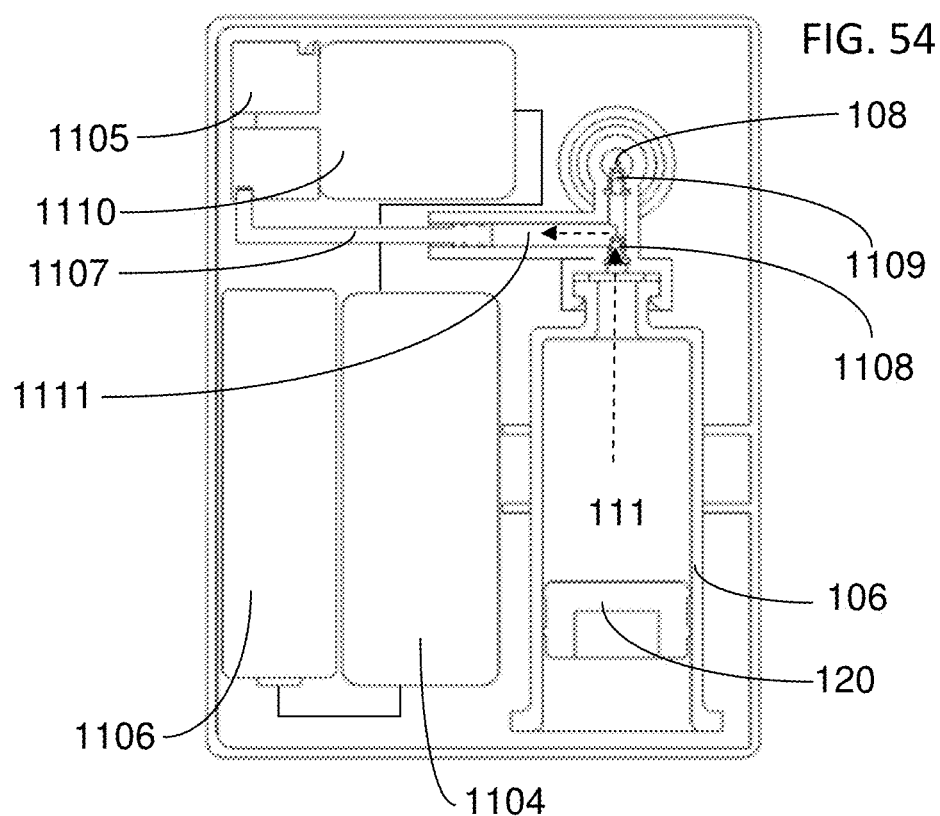
FIG. 54 is a cross-sectional view showing the medication is being drawn from a medication container into a piston pump of the tenth alternative infusion device assembly according to the invention.
Figure 55:
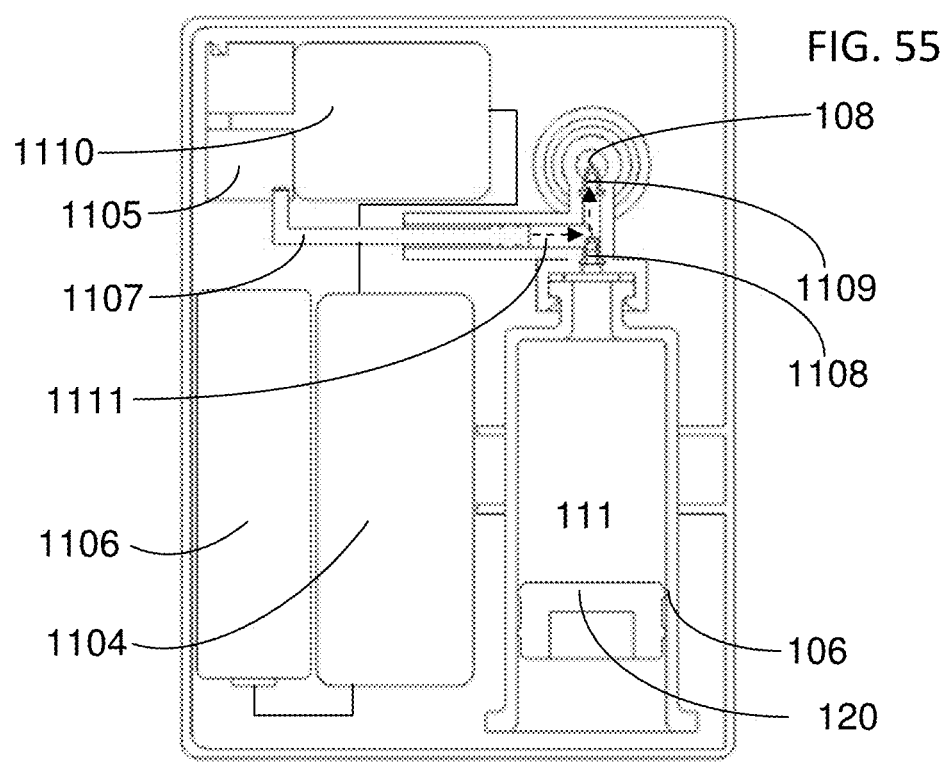
FIG. 55 is a cross-sectional view showing the medication is being dispensed from the piston pump chamber of the tenth alternative infusion device assembly according to the invention.
Figure 56:
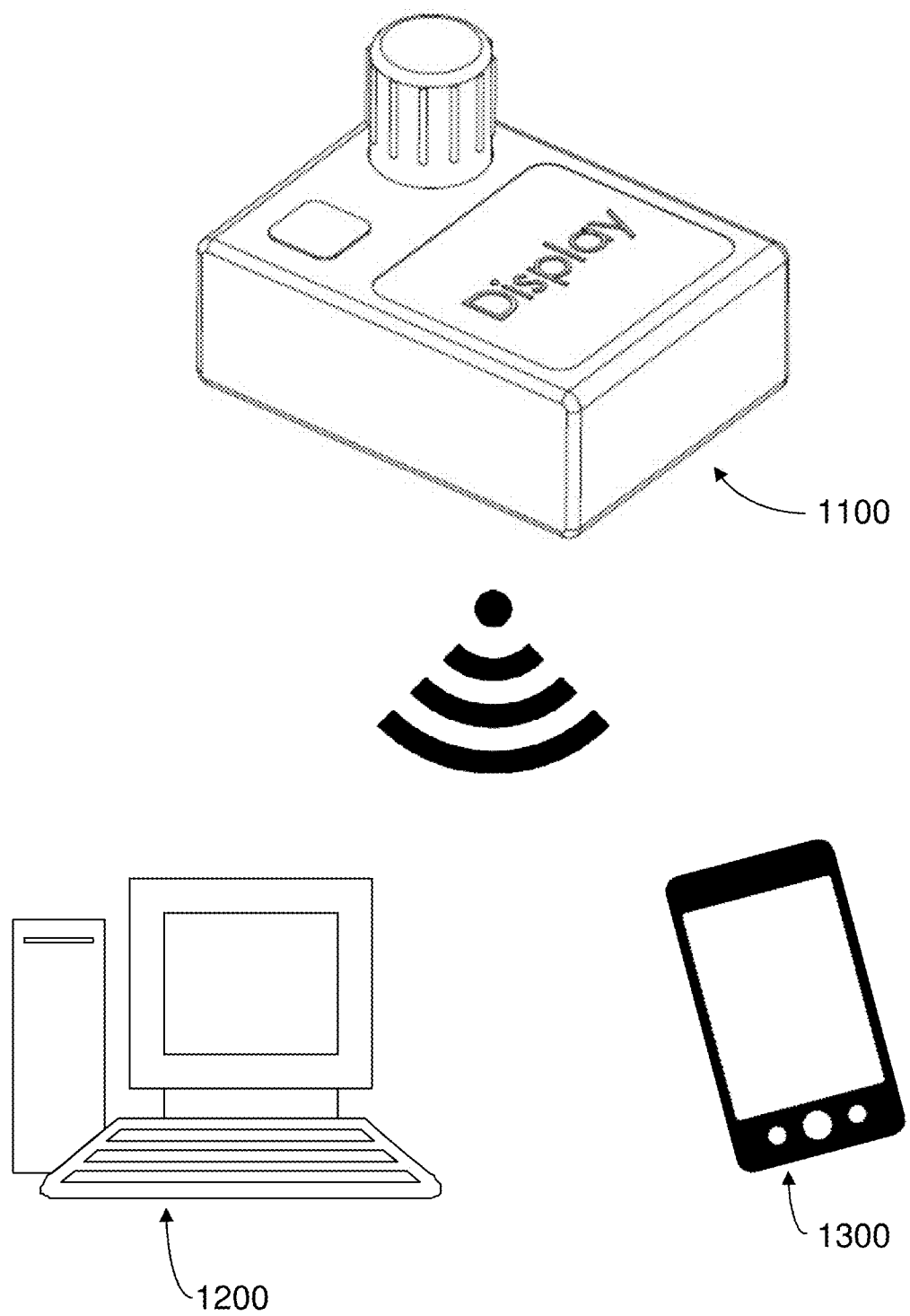
FIG. 56 shows a perspective view of a signal communication between the tenth alternative infusion device assembly according to the invention, and other information technology equipments.

FIGS. 52-56 illustrate the construction and function mechanism of the tenth alternative infusion device assembly 1100 according to the invention. The infusion device assembly 1100 has the same needle insertion mechanism 130 used in the infusion device assembly 10. Major components of the infusion device assembly 1100 including a housing 1101, an information display panel 1102, an power button 1103, a reciprocating pump (including a piston 1107, a pump chamber 1111 and one-way check valves 1108, 1109), a cam 1105, a cam driving motor 1110, a microcontroller 1104 and battery power supply 1106 and the needle insertion mechanism 130. With reference to FIGS. 53-55, the reciprocal movement of piston 1107 is controlled by the rotational movement of the cam 1105. The rotational movement of the cam 1105 is driven by the cam driving motor 1110. The microcontroller 1104 controls the rotation speed and duration of the cam 1105 through the cam driving motor 1110. FIG. 54 shows the infusion assembly device 1100 with the reciprocating pump at suction position, and FIG. 55 shows the infusion assembly device 1100 with the reciprocating pump at dispensing position. When the reciprocating pump is at suction position, the liquid medication 111 is withdrawn from the medication container 106 inward to the pump chamber 1111 through the one-way check valve 1108 while another check valve 1109 is closing. When the reciprocating pump is at dispensing position, the liquid medication 111 is dispensed from the pump chamber 1111 outward through the one-way check valve 1109 while another check valve 1108 is closing. Consequently, the liquid medication 111 is pushed out and delivered through the infusion needle 108. The desired medication infusion volume and rate can be set by inputting information on the information display panel 1102. Furthermore, the desired medication infusion volume and rate can be controlled and/or communicated through signal communication between the infusion device 1100 and other information technology equipment, such as computers 1200 or mobile devices 1300.

All the features in the above embodiments and design concepts herein can be inter-changed and combined to generate new device designs. Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A medication infusion device comprising:
a medication container containing liquid medication;
a reciprocating pump assembly comprising a pump chamber having a longitudinal axis and a piston, wherein the liquid medication is withdrawn from the medication container into the pump chamber during suction operation of the reciprocating pump assembly, and the liquid medication is dispensed out of the pump chamber during dispensing operation of the reciprocating pump assembly; and
a rotary motor based driving unit configured to move the piston linearly without rotation, wherein the rotary motor based driving unit does not move linearly together with the piston, and wherein the rotary motor based driving unit has a longitudinal axis and the longitudinal axis of the rotary motor based driving unit is not aligned with the longitudinal axis of the pump chamber.

2. The medication infusion device according to claim 1, further comprising an infusion needle.

3. The medication infusion device according to claim 1, further comprising a fluid control means preventing the liquid medication from flowing into the medication container during dispensing operation of the pump assembly.

4. The medication infusion device according to claim 1, further comprising a microcontroller to control medication infusion volume and rate.

5. The medication infusion device according to claim 1, wherein the medication container further comprising a movable medication container piston to seal the liquid medication in the medication container.

6. The medication infusion device according to claim 5, further comprising a spring applying push force on the movable medication container piston.

7. The medication infusion device according to claim 1, wherein the medication container is a pre-filled cartridge.

8. The medication infusion device according to claim 1, further comprising a connecting needle connecting the medication container and the pump chamber of the pump assembly.

9. The medication infusion device according to claim 1, wherein the rotary motor based driving unit operates through a cam.

10. The medication infusion device according to claim 1, further comprising a means to communicate with an external information technology equipment.

11. The medication infusion device as in claim 1, wherein the medication container has at least one rigid wall.

* * * * *